United States Patent
Denison et al.

(10) Patent No.: US 9,788,750 B2
(45) Date of Patent: Oct. 17, 2017

(54) SEIZURE PREDICTION

(75) Inventors: Timothy J. Denison, Minneapolis, MN (US); Wesley A. Santa, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 3243 days.

(21) Appl. No.: 11/799,051

(22) Filed: Apr. 30, 2007

(65) Prior Publication Data

US 2008/0269631 A1     Oct. 30, 2008

(51) Int. Cl.
| | |
|---|---|
| *A61B 5/04* | (2006.01) |
| *A61B 5/053* | (2006.01) |
| *A61B 5/0478* | (2006.01) |
| *A61B 5/00* | (2006.01) |
| *A61B 5/024* | (2006.01) |
| *A61B 5/0402* | (2006.01) |
| *A61B 5/0488* | (2006.01) |

(Continued)

(52) U.S. Cl.
CPC ............ *A61B 5/053* (2013.01); *A61B 5/0478* (2013.01); *A61B 5/4094* (2013.01); *A61B 5/4839* (2013.01); *A61B 5/7275* (2013.01); *A61B 5/024* (2013.01); *A61B 5/0402* (2013.01); *A61B 5/0488* (2013.01); *A61B 5/7228* (2013.01); *A61N 1/08* (2013.01); *A61N 1/36025* (2013.01); *A61N 1/36082* (2013.01)

(58) Field of Classification Search
CPC ...... A61B 5/0478; A61B 5/4094; A61B 5/503
USPC .................................................. 600/544, 545
See application file for complete search history.

(56) References Cited

U.S. PATENT DOCUMENTS

| | | |
|---|---|---|
| 3,130,373 A | 4/1964 | Braymer |
| 3,993,046 A | 11/1976 | Fernandez et al. |
| 4,177,819 A | 12/1979 | Kofsky et al. |

(Continued)

FOREIGN PATENT DOCUMENTS

| | | |
|---|---|---|
| EP | 0 354 060 | 2/1990 |
| GB | 1 249 395 | 10/1971 |

(Continued)

OTHER PUBLICATIONS

Holder, "Electrrical Impedance Tomography (EIT) of Brain Function". Brain Topography, vol. 5, No. 2, 1992.*

(Continued)

*Primary Examiner* — Christian Jang
(74) *Attorney, Agent, or Firm* — Shumkaer & Sieffert, P.A.

(57) ABSTRACT

Seizure prediction systems and methods include measuring impedance within a brain of a patient to determine whether the brain is in a state indicative of a possibility of an onset of a seizure. In some embodiments, the measured impedance is compared to a predetermined threshold in order to determine whether the brain is in a state indicative of a possibility of a seizure. In other embodiments, a trend of the impedance measurements is correlated to a template. In other embodiments, a frequency component of a waveform of the impedance measurement amplitudes over time is correlated to frequency components of a template waveform. Upon detecting a state in which a seizure is likely to occur, a seizure indicator may be generated, which, in some embodiments, may be used to activate therapy delivery to the patient or, in other embodiments, activate an alarm.

56 Claims, 16 Drawing Sheets

(51) Int. Cl.
*A61N 1/08* (2006.01)
*A61N 1/36* (2006.01)

(56) References Cited

U.S. PATENT DOCUMENTS

| | | | |
|---|---|---|---|
| 4,188,586 A | 2/1980 | Egami | |
| 4,214,591 A | 7/1980 | Sato et al. | |
| 4,566,464 A | 1/1986 | Piccone et al. | |
| 4,933,642 A | 6/1990 | Lee | |
| 5,061,593 A | 10/1991 | Yoerger et al. | |
| 5,113,143 A | 5/1992 | Wei | |
| 5,179,947 A | 1/1993 | Meyerson et al. | |
| 5,311,876 A | 5/1994 | Olsen et al. | |
| 5,477,481 A | 12/1995 | Kerth | |
| 5,663,680 A | 9/1997 | Nordeng | |
| 5,807,270 A | 9/1998 | Williams | |
| 5,928,272 A | 7/1999 | Adkins et al. | |
| 5,995,868 A | 11/1999 | Dorfmeister et al. | |
| 6,016,449 A | 1/2000 | Fischell et al. | |
| 6,061,593 A | 5/2000 | Fischell et al. | |
| 6,064,257 A | 5/2000 | Sauer | |
| 6,130,578 A | 10/2000 | Tang | |
| 6,262,626 B1 | 7/2001 | Bakker et al. | |
| 6,360,123 B1 | 3/2002 | Kimchi et al. | |
| 6,456,159 B1 | 9/2002 | Brewer | |
| 6,473,639 B1 | 10/2002 | Fischell et al. | |
| 6,584,351 B1 | 6/2003 | Ekwall | |
| 6,671,555 B2 * | 12/2003 | Gielen et al. | 607/45 |
| 6,810,285 B2 | 10/2004 | Pless et al. | |
| 7,006,872 B2 | 2/2006 | Gielen et al. | |
| 7,098,823 B2 | 8/2006 | O'Dowd et al. | |
| 7,146,218 B2 | 12/2006 | Esteller et al. | |
| 7,233,198 B2 | 6/2007 | Niederkorn | |
| 7,391,257 B1 | 6/2008 | Denison et al. | |
| 2002/0082514 A1 | 6/2002 | Williams et al. | |
| 2003/0004428 A1 | 1/2003 | Pless et al. | |
| 2003/0006782 A1 | 1/2003 | Shambroom et al. | |
| 2003/0146786 A1 | 8/2003 | Gulati et al. | |
| 2004/0138536 A1 | 7/2004 | Frei et al. | |
| 2004/0141558 A1 | 7/2004 | Plisch et al. | |
| 2005/0081847 A1 | 4/2005 | Lee et al. | |
| 2005/0165323 A1 | 7/2005 | Montgomery et al. | |
| 2006/0055456 A1 | 3/2006 | Niederkorn | |
| 2006/0135877 A1 | 6/2006 | Giftakis et al. | |
| 2006/0139192 A1 | 6/2006 | Morrow et al. | |
| 2006/0139193 A1 | 6/2006 | Morrow et al. | |
| 2006/0173501 A1 | 8/2006 | Stickney et al. | |
| 2006/0173510 A1 | 8/2006 | Besio et al. | |
| 2006/0264777 A1 | 11/2006 | Drew | |
| 2006/0293720 A1 | 12/2006 | DiLorenzo | |
| 2012/0220890 A1 | 8/2012 | Asirvatham et al. | |

FOREIGN PATENT DOCUMENTS

| | | |
|---|---|---|
| WO | WO 02/01711 A1 | 1/2002 |
| WO | WO 02/03087 A1 | 1/2002 |
| WO | WO 2006/019822 | 2/2006 |
| WO | WO 2006/066098 | 6/2006 |
| WO | WO 2007/124189 A1 | 11/2007 |

OTHER PUBLICATIONS

Bakker et al., "A CMOS Nested-Chopper Instrumentation Amplifier with 100-nV Offset," IEEE Journal of Solid-State Circuits, vol. 35, No. 12, pp. 1877-1883, Dec. 2000.
Boser, "Capacitive Interfaces for Monolithic Integrated Sensors," Chapter in "RF Analog-to-Digital Converters; Sensor and Actuator Interfaces; Low-Noise Oscillators, PLLs and Synthesizers," R.J. van de Plassche, J.H. Huijsing, and W.M.C. Sansen (eds.), Kluwer Academic Publishers, Nov. 1997.
Martins et al., "A CMOS IC for Portable EEG Acquisition Systems," IEEE Transactions on Instrumentation and Measurement, vol. 47, No. 5, pp. 1191-1196, Oct. 1998.
Office Action dated May 16, 2012 for U.S. Appl. No. 11/799,031, (12 pgs.).
Elazar et al., "Impedance Changes during Epileptic Seizures," Epilepsia, 7, pp. 291-307 (1966).
Denison et al., "A 2.2 µW 94nV/√Hz, Chopper-Stabilized Instrumentation Amplifier for EEG Detection in Chronic Implants," ISSCC 2007, Session 8, Biomedical Devices, 8.6, Feb. 13, 2007 (3 pgs.).
Notification of Transmittal of the International Search Report and the Written Opinion of the International Search Authority, or the Declaration dated Apr. 28, 2008 for PCT/US2007/010393 (15 pgs.).
International Preliminary Report on Patentability dated Nov. 12, 2009 for PCT Application No. PCT/US2007/010393 (9 pgs.).
Sanduleanu et al., "A Low Noise, Low Residual Offset, Chopped Amplifier for Mixed Level Applications," IEEE, 0-7803-5008-1/98, pp. 333-336, 1998.
Hadiashar et al., "A Chopper Stabilized CMOS Analog Multiplier with Ultra Low DC Offsets," Solid-State Circuits Conference, pp. 364-367, 2006.
Yiqian Ying, "Chopper Stabilized Amplifiers," Term Paper, Department of Electrical and Computer Engineering, University of Toronto, 17 pgs., 2001.
Enz et al., "Circuit Techniques for Reducing the Effects of Op-Amp Imperfections; Autozeroing, Correlated Double Sampling, and Chopper Stabilization," Proceedings of the IEEE, vol. 84, No. 11, pp. 1584-1614 (1996).
Yazicioglu et al., "A 60uW 60nV/rtHz Readout Front-End for Portable Biopotential Acquisition Systems," ISSCC Digest of Technical Papers 2006, paper 2.6., 4 pgs.
Makinwa, "Dynamic Offset Cancellation Techniques," Smart Sensor Systems 2002, 42 pgs.
Ng et al., "A CMOS Analog Front-End IC for Portable EEG/ECG Monitoring Applications," IEEE Trans. on Circuits and Systems, vol. 52 No. 11, (Nov. 2005), pp. 2335-2347.
Burt et al., "A Micropower Chopper-Stabilized Operational Amplifier using an SC Notch Filter with Synchronous Integration inside the Continuous-Time Signal Path," ISSCC Digest of Technical Papers 2006, paper 19.6., 2 pgs.
Harrison et al., "A Low-Power Low-Noise CMOS Amplifier for Neural Recording Applications," IEEE J. of Solid-State Circuits, vol. 38, No. 6, pp. 958-965, 2003.
Wu et al., "A 1V 2.3 µW Biomedical Signal Acquisition IC," ISSCC Digest of Technical Papers 2006, paper 2.7. 2 pgs.
Harrison et al., "A Low-Power Integrated Circuit for a Wireless 100-Electrode Neural Recording System," ISSCC Digest of Technical Papers 2006, paper 30.2, 2 pgs.
Harrison et al., "Local Field Potential Measurement with Low-Power Analog Integrated Circuit", Engineering in Medicine and Biology Society, 2004. IEMBS apos; 04, 26th Annual International Conference of the IEEE, vol. 2, Issue , pp. 4067-4070 vol. 6, Sep. 1-5, 2004.
U.S. Appl. No. 11/700,738, filed Jan. 31, 2007, entitled "Chopper-Stabilized Instrumentation Amplifier for Wireless Telemetry," by Denison.
U.S. Appl. No. 11/700,404, filed Jan. 31, 2007, entitled "Chopper-Stabilized Instrumentation Amplifier for Wireless Telemetry," by Denison.
U.S. Appl. No. 11/700,405, filed Jan. 31, 2007, entitled "Chopper-Stabilized Instrumentation Amplifier for Impedance Measurement," by Denison et al.
U.S. Appl. No. 11/799,031, filed Apr. 30, 2007, entitled "Seizure Prediction," by Santa et al.
U.S. Appl. No. 11/741,111, filed Apr. 27, 2007, entitled "Method for Improving Seizure Detection Using an ECG", Giftakis et al.
U.S. Appl. No. 11/741,103, filed Apr. 27, 2007, entitled "Method for Improving Seizure Detection Using an ECG", Giftakis et al.
U.S. Appl. No. 11/609,388, filed Dec. 12, 2006, entitled "Implantable Seizure Detection Algorithm," by Panken et al.
Sanduleanu et al,, "A Low Noise, Low Residual Offset, Chopped Amplifier for Mixed Level Applications," IEEE, 0-7803-5008-1/98, pp. 333-336, Sep. 1998.

(56) References Cited

OTHER PUBLICATIONS

Hadiashar et al., "A Chopper Stabilized CMOS Analog Multiplier with Ultra Low DC Offsets," Solid-State Circuits Conference, pp. 364-367, Sep. 2006.

Yiqian Ying, "Chopper Stabilized Amplifiers," Term Paper, Department of Electrical and Computer Engineering University of Toronto, 17 pgs., Nov. 12, 2001.

Enz et al., "Circuit Techniques for Reducing the Effects of Opamp Imperfections," Proc. of the IEEE vol. 84, No. 11, pp. 1584-1614, Nov. 1996.

Yazicioglu et al., "A 60uW 60nV/rtHz Readout Front-End for Portable Biopotential Acquisition Systems," ISSCC Digest of Technical Papers 2006, paper 2.6, Feb. 2006.

Makinwa, "Dynamic Offset Cancellation Techniques," Smart Sensor Systems '02, May 2002.

Ng et al., "A CMOS Analog Front-End IC for Portable EEG/ECG Monitoring Applications," IEEE Trans. on Circuits and Systems, vol. 52 No. 11, Nov. 2005.

Burt et al., "A Micropower Chopper-Stabilized Operational Amplifier using an SC Notch Filter with Synchronous Integration inside the Continuous-Time Signal Path," ISSCC Digest of Technical Papers 2006, paper 19.6, Feb. 2006.

Harrison et al., "A Low-Power Low-Noise CMOS Amplifier for Neural Recording Applications," IEEE J. of Solid-State Circuits, vol. 38, No. 6, pp. 958-965, Jun. 2003.

Wu et al., "A 1V 2.3mW Biomedical Signal Acquisition IC," ISSCC Digest of Technical Papers 2006, paper 2.7, Feb. 2006.

Harrison et al., "A Low-Power Integrated Circuit for a Wireless 100-Electrode Neural Recording System," ISSCC Digest of Technical Papers 2006, paper 30.2, Feb. 2006.

Office Action from U.S. Appl. No. 11/799,031, dated Sep. 17, 2012, 9 pp.

Response to Final Office Action dated Sep. 17, 2012, from U.S. Appl. No. 11/799,031, filed Dec. 10, 2012, 17 pp.

Responsive Amendment dated Aug. 14, 2012 for U.S. Appl. No. 11/799,031, (20 pgs.).

Office Action from U.S. Appl. No. 11/799,031, dated Mar. 4, 2013, 5 pp.

Response to Office Action dated Mar. 4, 2013, from U.S. Appl. No. 11/799,031, filed Jun. 4, 2013, 17 pp.

\* cited by examiner

SEIZURE PREDICTION

TECHNICAL FIELD

The invention relates to physiological monitoring and, more particularly, physiological monitoring of the brain for seizure prediction.

BACKGROUND

Epilepsy is a neurological disorder characterized by the occurrence of seizures, although seizures may also occur in persons who do not have epilepsy. Seizures are typically attributable to abnormal electrical activity of a group of brain cells. A seizure may occur when the electrical activity of certain regions of the brain, or even the entire brain, becomes abnormally synchronized. The onset of a seizure may be debilitating. For example, the onset of a seizure may result in involuntary changes in body movement, body function, sensation, awareness or behavior (e.g., an altered mental state). In some cases, each seizure may cause some damage to the brain, which may result in progressive loss of brain function over time.

Attempts to manage seizures have included the delivery of electrical stimulation to regions of the brain and/or the delivery of drugs either orally or infused directly into regions of the brain. In electrical stimulation systems, a medical lead is implanted within a patient and coupled to an external or implanted electrical stimulator. The target stimulation site within the brain or elsewhere may differ between patients, and may depend upon the type of seizures being treated by the electrical stimulation system. In some therapy systems, electrical stimulation is continuously delivered to the brain. In other systems, the delivery of electrical stimulation is triggered by the detection or prediction of some event, such as the detection of a seizure by electroencephalogram (EEG) sensors within the brain.

In automatic drug delivery systems, a catheter is implanted within a patient and coupled to an external or implanted fluid delivery device. The fluid delivery device may deliver a bolus of an anti-seizure drug into the blood stream or into a region of the brain of the patient at regular intervals, upon the detection or prediction of some event, such as the detection of a seizure by EEG sensors implanted within the brain, or at the direction of the patient or clinician.

SUMMARY

In general, the invention involves techniques for monitoring the impedance of one or more regions of the brain of a patient to predict the likelihood of an onset of a seizure. It is believed that the impedance of one or more regions of the brain, or even the entire brain, is indicative of a physiological state of the brain, and may be monitored to determine whether the brain of a patient is primed for a seizure. That is, impedance of one or more regions of the brain may indicate whether an onset of a seizure is likely or whether a seizure is in progress. In some embodiments, the relationship between the measured impedance of the brain and an absolute threshold impedance value may be used to predict a seizure. For example, if an amplitude of the impedance signal is greater than or equal to a predetermined threshold, the brain may be in a state that indicates the possibility of the onset of a seizure.

In other embodiments, a measured impedance signal may be analyzed for slope, amplitude, temporal correlation or frequency correlation with a template signal, or combinations thereof in order to determine whether a seizure is likely to occur. For example, a trend in the measured impedance values may be compared to a predetermined template. For example, if rate of change (i.e., the slope) of the measured impedance over time correlates to the slope of a trend template, the brain may be in a state in which a seizure is likely. Alternatively, if inflection points in the impedance signal waveform substantially correlate to a template, the brain may be in a state in which a seizure is likely. Embodiments employing a temporal correlation technique may sample an impedance signal with a sliding window and compare the sample to a template to identify a signal that correlates well with the template. Embodiments employing a frequency correlation technique may include analyzing the impedance signal in the frequency domain to compare selected frequency components of the impedance signal to corresponding frequency components of the template signal.

Upon predicting the onset of a seizure by monitoring the impedance of one or more regions of the brain, therapy may be delivered to the patient in an attempt to prevent the seizure or mitigate the effects of the seizure. For example, electrical stimulation therapy or drug therapy may be delivered to the patient to return the brain to a state in which a seizure is less likely, thereby inhibiting the onset of the seizure and/or reducing the severity and/or duration of the seizure. In this way, impedance monitoring of the brain may be incorporated into a closed loop system for treating seizures. In addition or instead of delivering therapy, a an alarm may be provided upon the prediction of a seizure.

In one embodiment, the invention is directed to a method comprising measuring an impedance of a brain of a patient and determining whether the brain is in a state indicative of a possibility of seizure based on the measured impedance.

In another embodiment, the invention is directed to a system comprising one or more electrodes implantable in a brain of a patient, an impedance sensing module that delivers an electrical stimulus to the brain via the electrodes to measure an impedance of the brain, and a processor coupled to the impedance sensing module. The processor receives impedance measurements from the impedance sensing module and determines whether the brain is in a state indicative of a possibility of seizure based on the measured impedance.

In another embodiment, the invention is directed to a system comprising means for measuring an impedance of a brain of the patient and means for determining whether the measured impedance indicates the brain is in a state indicative of a possibility of seizure.

In another embodiment, the invention is directed to a computer-readable medium containing instructions. The instructions cause a programmable processor receive a signal indicative of a measured impedance of a brain of a patient and determine whether the brain is in a state indicative of a possibility of seizure based on the measured impedance.

In another embodiment, the invention is directed to a method comprising measuring an impedance of a brain of a patient, detecting an occurrence of a seizure, associating the occurrence of the seizure with at least one impedance measurement, and recording the at least one impedance measurement associated with the occurrence of the seizure.

In another embodiment, the invention is directed to a system comprising an impedance sensing module that measures an impedance of a brain of a patient, a seizure detection module that detects an occurrence of a seizure, a memory, and a processor coupled to the impedance sensing module and the seizure detection module. The processor associates the occurrence of the seizure with at least one impedance measurement and records the at least one impedance measurement associated with the occurrence of the seizure in the memory.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
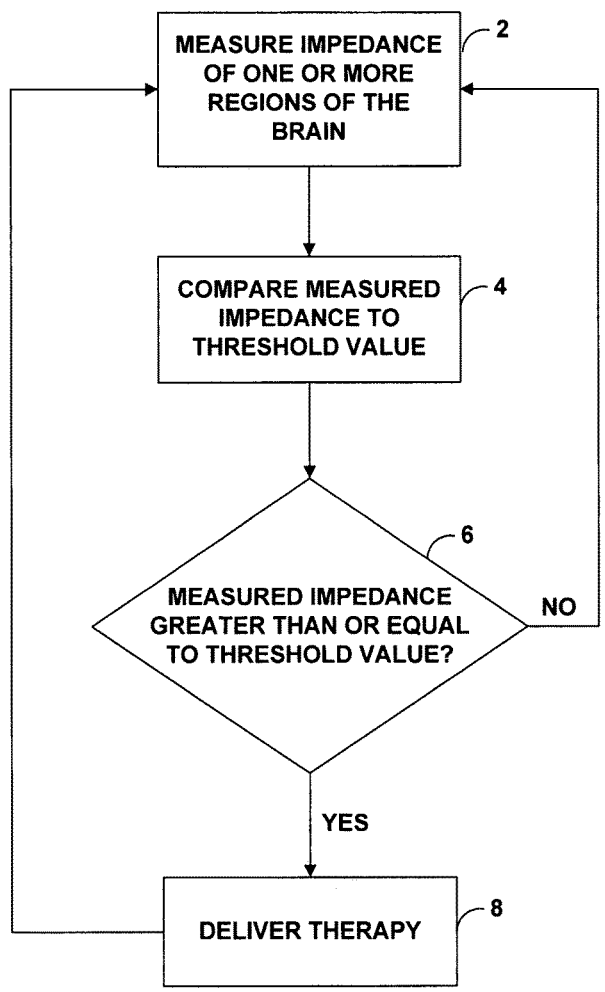
FIG. 1A is a flow diagram illustrating a method for predicting seizure in a patient by measuring an impedance of the brain of the patient and comparing the measured impedance to a threshold value.

Therapy delivery systems may be used to treat seizures to mitigate the effects of the seizure, shorten the duration of the seizure or to prevent the onset of seizures. In therapy systems in which the therapy (e.g., a drug or electrical stimulation) is delivered in response to the detection or prediction of a seizure, the timing of the therapy delivery is important to the efficacy of the therapy. The time required to analyze the input signals from sensors that are used to detect the seizure and produce an output which triggers the delivery of therapy are important factors in providing a warning to the patient of the onset of seizures, intervention of seizures or prevention of seizures. It is generally desirable to predict the onset of a seizure and deliver therapy to treat the seizure before the patient feels any effects (e.g., auras, changing in muscle tone, etc.) of the seizure or before any symptoms are seen by an observer. In addition, it is desirable to limit the number of false positives (i.e., the incorrect detection of a seizure), and false negatives (i.e., the failure to detect a seizure).

It is believed that the impedance of one or more regions of the brain, or even the entire brain, is indicative of a physiological state of the brain, and may be monitored to determine whether the brain of a patient is primed for a seizure. In particular, it is believed that the impedance of the brain is indicative of the electrochemical state and/or fluid distribution of the brain, which are both related to the onset of seizures. Certain impedance values within the brain may indicate that the brain is in a "bias" state, and that a seizure is likely to occur (i.e., there is a high probability of seizure). This bias state may occur just prior to an onset of a seizure when the brain is in a state in which a seizure is likely to occur. Thus, the bias state may be indicative of a state within the brain indicative of a possibility of a seizure.

The present invention involves monitoring and analyzing impedance measurements of the brain to predict a seizure. Based on the prediction of a seizure, therapy may be delivered to a patient to help prevent the seizure or reduce the severity or duration of the seizure. In addition to the therapy delivery or instead of the therapy delivery, an alarm may be provided upon the prediction of the seizure, for example, to alert the patient to the possibility of an onset of a seizure. It is believed that detecting seizures by monitoring the impedance of the brain may help reduce the amount of delay before therapy is initiated compared to systems that rely on EEG sensing because changes in impedance of one or more regions of the brain may be an earlier indicator of the likelihood of a seizure.

Neurological disorders that cause seizures, such as epilepsy, may be generated in one or more of regions of the brain, which may differ between patients. The impedance in one or more of these "key regions" of the brain may be monitored. These "key regions" of the brain may be, for example, regions of the brain to which therapy is delivered in order to treat or prevent seizures. Examples of key regions of the brain include, but are not limited to, the cortex (e.g., front or motor cortex), brain stem, cranial nerves (e.g., the vagus nerve), or deep brain regions, such as the anterior thalamus, ventrolateral thalamus, globus pallidus, substantia nigra pars reticulata, subthalamic nucleus, neostriatum, cingulated gyrus or the cingulate gyrus.

As described in further detail below, an impedance signal may be analyzed using any suitable technique in order to determine whether the brain is in a state in which a seizure is likely to occur. For example, the instantaneous or average amplitude of impedance over a period of time may be compared to amplitude threshold. As another example, a slope of the amplitude of the signal over time may be compared to trend information or timing between inflection points or other critical points in the pattern of the amplitude of the impedance signal over time may be compared to trend information. As another example, the impedance waveform may be sampled with a sliding window and a correlation may be performed between the waveform and a stored template waveform. As another example, an amplitude of frequency components of the impedance waveform may be analyzed and compared to frequency components of template waveform.

FIG. 1A is a flow diagram illustrating a method for predicting the onset of a seizure in a patient by measuring an impedance of the brain of the patient. The complex impedance of the brain of the patient is measured via an impedance sensing device, which may be implanted or may include both external and implanted components (2). In one embodiment, the impedance sensing device measures the impedance substantially continuously. In another embodiment, the impedance sensing device intermittently measures the impedance at a measurement frequency, such as, but not limited to, a frequency of about one hertz (Hz) to about 100 Hz.

Figure 6:
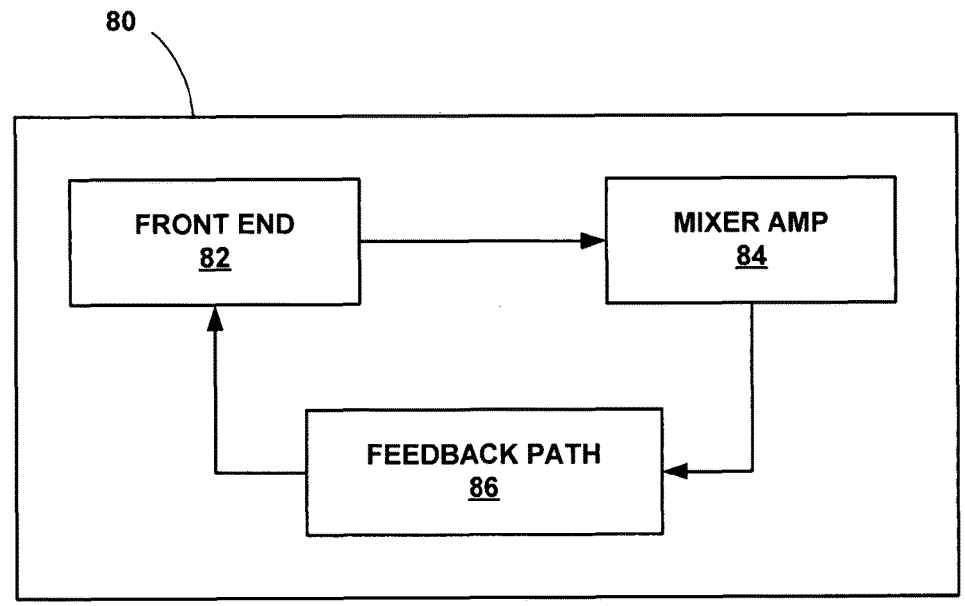
FIG. 6 is a block diagram illustrating an embodiment of a chopper-stabilized instrumentation amplifier, which may be incorporated into a medical device for measuring the impedance of a brain of a patient.
Figure 7:
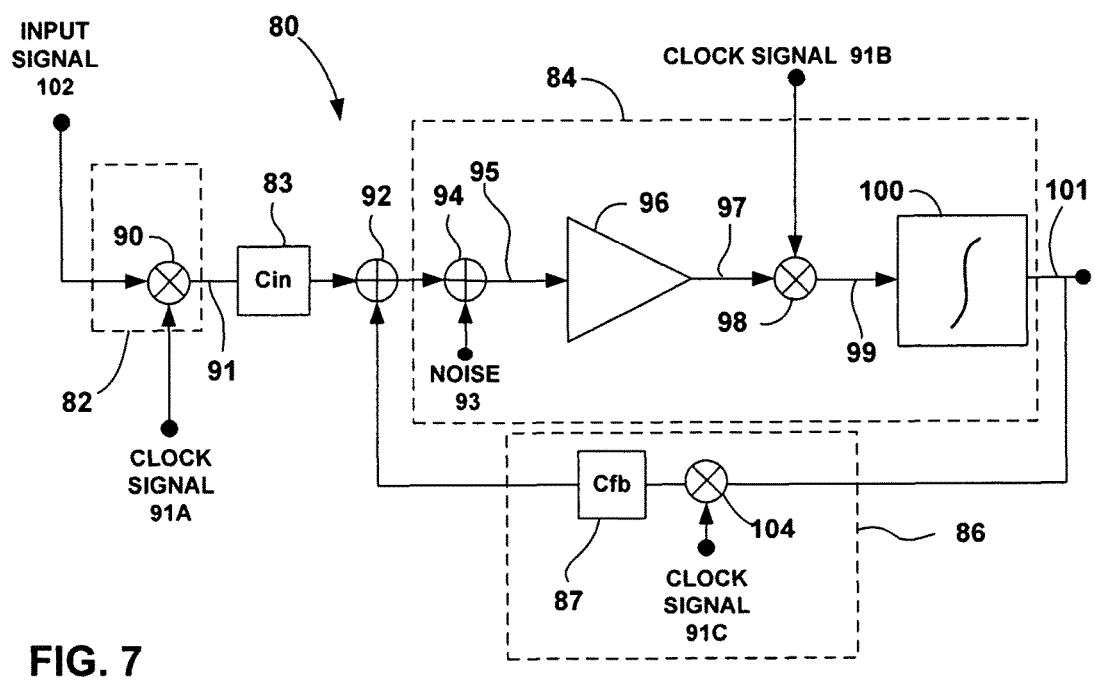
FIG. 7 is a block diagram illustrating a signal path flow of one embodiment of instrumentation amplifier that may be incorporated into an impedance sensing module of a medical device.
Figure 8:
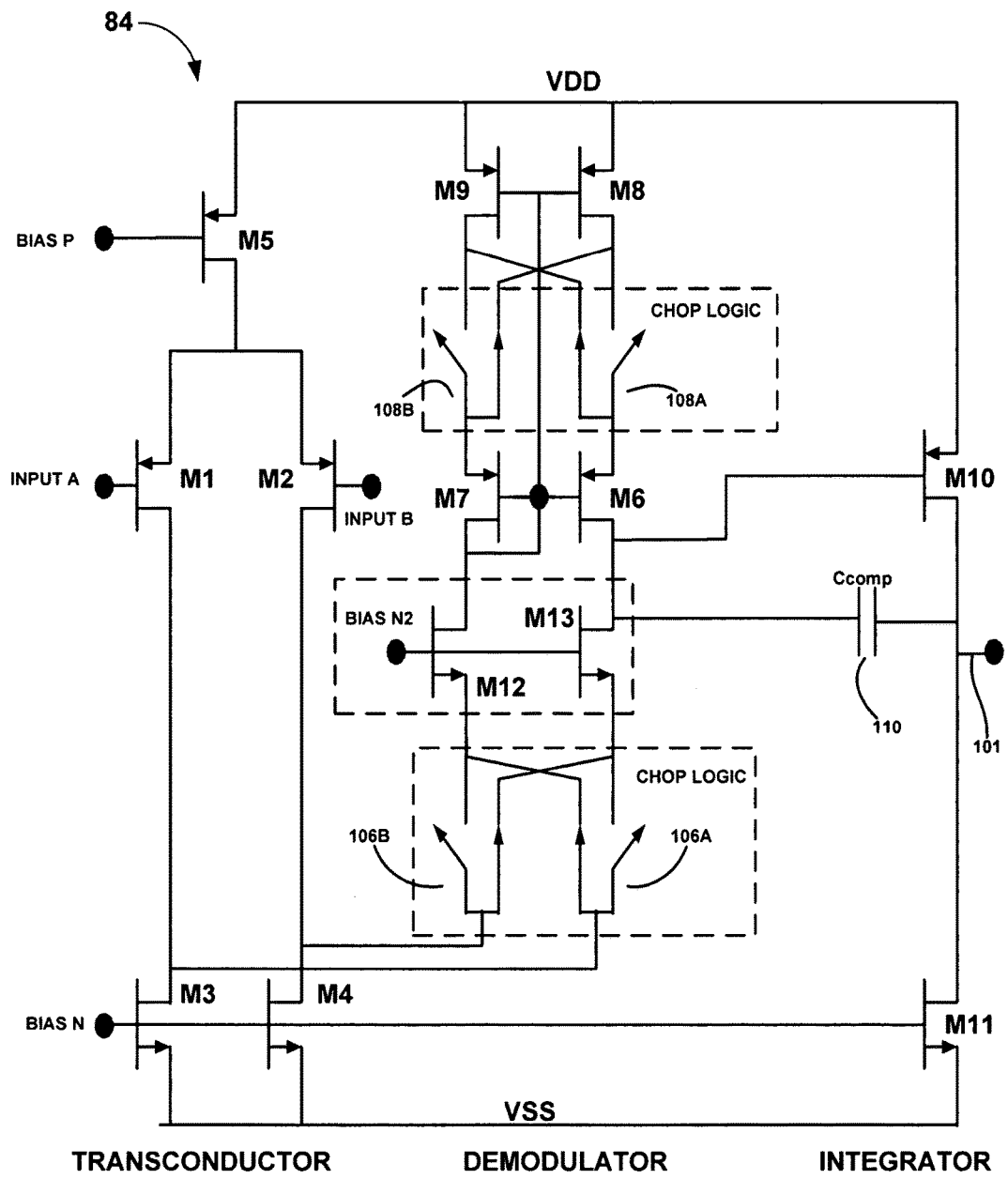
FIG. 8 is a circuit diagram illustrating a chopper-stabilized mixer amplifier forming part of an instrumentation amplifier.

Embodiments of a chopper stabilized instrumentation amplifier that may be incorporated into an impedance sensing device to amplify and filter sensor outputs are shown in FIGS. 6-8, and described below. The chopper stabilized instrumentation amplifier may provide low noise measurement and help decrease the power consumption of the impedance sensing device, enabling the impedance sensing device to measure the impedance of the brain substantially continuously while still operating for several months or years relying on power from a finite power source, such as a rechargeable or non-rechargeable battery.

Figure 2A:
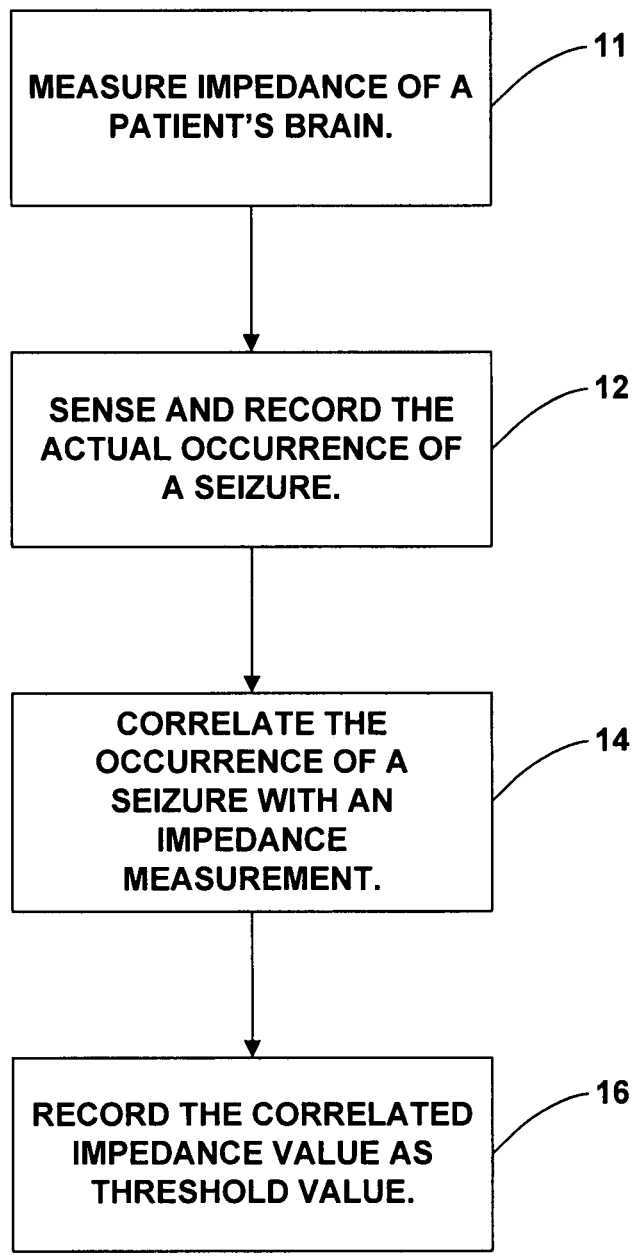
FIG. 2A is a flow diagram illustrating a technique for determining one or more threshold values to compare to impedance measurements in order to predict a seizure.
Figure 2B:
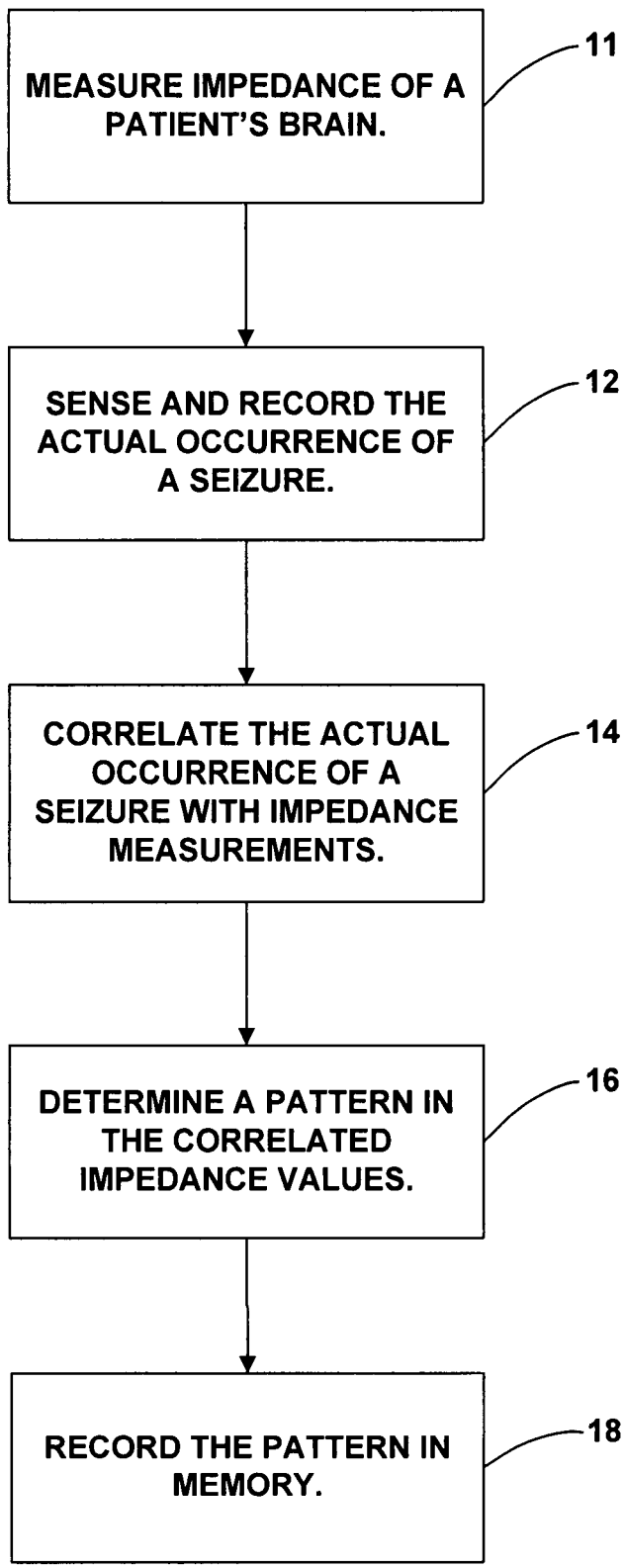
FIG. 2B is a flow diagram illustrating a technique for determining one or more trend templates to compare to a pattern of impedance measurements in order to predict a seizure.

In order to measure the impedance of the brain, at least two electrodes are implanted within the relevant region(s) of the brain and coupled to an impedance sensing circuit. The relevant region(s) of the brain may be determined in a trial phase that precedes chronic implantation of the impedance sensing device and therapy delivery device. An example of a trial phase is shown in FIGS. 2A-B. Complex impedance is a measure of the opposition to the stimulation current. Thus, stimulation current is delivered to the brain via the implanted electrodes in order to measure impedance of the brain.

The stimulation current may be relatively low to prevent inadvertent stimulation of tissue and to prevent the patient from feeling the stimulation current. For example, the stimulation current may be in a range of about 500 nanoamps (nA) to about 10 microamps (µA), although other stimulation currents may be used. The stimulation current that is delivered to measure impedance differs from that used to deliver stimulation therapy to the patient to prevent a seizure from occurring or to mitigate the effects of a seizure. In general, the stimulation current used for impedance measuring is at a relatively low current level and relatively high frequencies. Examples of frequencies that may be used for the input stimulation current to measure impedance of the brain include, but are not limited to range of about 1 kilohertz (kHz) to about 100 kHz, such as a range of about 4 kHz to about 16 kHz. In one embodiment, the stimulation current to measure impedance of the brain is about 12 kHz. Using stimulation currents having relatively high frequencies (e.g., 4 kHz or greater) to measure impedance helps prevent interference with other electrodes that may be implanted within the patient for delivery of electrical stimulation therapy or for sensing other physiological parameters, such as electroencephalogram (EEG) sensing.

It is believed that some frequency ranges may be more revealing of the impedance state of the region(s) of the brain for a particular patient than other frequency ranges. Thus, the impedance for the brain of a patient may be measured using stimulation currents modulated at frequencies in different frequency ranges. In addition, the optimal stimulation current frequency that is delivered to measure impedance of the brain may differ between patients and may depend on the region of the brain in which the impedance is measured.

The amplitude of the measured impedance signal is compared to a predetermined threshold (4). The relevant amplitude may be, for example, the instantaneous amplitude of an incoming impedance signal or an average amplitude of impedance over period of time. In one embodiment, the threshold value is determined during the trial phase that precedes implantation of a chronic therapy delivery device within the patient. In one embodiment, if the measured impedance is less than the threshold value (6), therapy is not delivered to the patient and the medical device continues measuring the impedance of the brain (2). On the other hand, if the measured impedance is greater than or equal to the threshold value (6), therapy is delivered to the patient in order to prevent the onset of the seizure, for example, by bringing the brain state to a "normal" state, i.e., a state in which a seizure is not likely to occur (8). The therapy may be delivered to the patient via a therapy delivery device that is separate from the impedance sensing device that measures the impedance. In other embodiments, a single medical device incorporates both a therapy delivery module and an impedance sensing device. In addition to or instead of delivering therapy to the patient, a patient alarm may be triggered in response to a measured impedance exceeding or equaling a threshold. Upon the impedance measurement exceeding or equaling a threshold, other actions may be triggered. For example, an implanted medical device or an external device, such as an external programming device may also record date and time of the impedance measurements and/or the actual impedance measurements for future analysis by a clinician.

In some cases, the delivery of therapy may not inhibit the onset of the seizure, but may reduce the severity and/or duration of the seizure. While it is believed that an impedance value greater than or equal to a threshold value may be an indicator of an imminent seizure, in some cases, a measured impedance that is less than or equal to a threshold value may indicate an imminent seizure. In such cases, therapy is triggered if the measured impedance is less than or equal to the threshold value. Hence, the measured impedance may be compared to a threshold value to determine whether the impedance is greater than or less than the threshold value, as applicable for particular therapy criteria. After therapy is delivered to the patient (8), the medical device continues measuring the impedance (2). This closed loop may continue indefinitely. Alternatively, the current delivered to measure the impedance of the one or more regions of the brain may be applied for a limited period of time, such as periodically during relevant times during the day, or the algorithm employed by the medical device to measure the impedance and determine whether the impedance indicates a state within the brain that is indicative of a possibility of a seizure within the brain.

Typically, at least a part of the therapy delivery device is implanted within the patient. For example, if the therapy delivery device is an electrical stimulator, one or more medical leads including one or more electrodes for delivering electrical stimulation to the target tissue site within the body (e.g., brain) of the patient may be implanted within the patient and positioned to deliver stimulation directly to one or more regions of the brain. The one or more medical leads may also carry the electrodes used for measuring the impedance of the brain. Alternatively, one or more of the measurement electrodes may be deployed via different lead or formed on a housing associated with an implanted electrical stimulator or implanted sensing device, each of which may be referred to as an implantable medical device (IMD). As mentioned previously, electrical stimulator and sensing component may be combined in a common IMD. An electrical stimulator may be implanted within the patient or may be carried externally. If the electrical stimulator is implanted, the stimulator housing may include one or more electrodes for delivering electrical stimulation and/or sensing impedance.

In each of the embodiments discussed herein that include a medical device that is implanted in the patient's body, the implant site may be any suitable location, such as, but not limited to, in a pectoral region, upper back, lower back, lower abdomen, or buttocks. Alternatively, the medical device may be a cranial implant.

In another embodiment, in addition to or instead of delivering therapy to the patient when the measured impedance equals or exceeds a threshold value, a medical device may generate an alarm to indicate that there is an increased probability of a seizure. The alarm may be, for example, in the form of an audible sound, visual alert (e.g., a flashing light), a tactile alert (e.g., a mechanical vibration) or a combination of the audible, visual, and/or tactile alerts. Alternatively, other alerting techniques may be employed. The patient alarm may be useful if the patient is involved in an activity in which the patient and/or another person would be placed in a potentially harmful or compromising position if the patient experienced a seizure. The patient alarm may provide the patient with enough time to take measures to prevent any harm to himself or another person. For example, if the patient receives the seizure alarm while driving, the patient may pull over at the nearest available spot.

Figure 1B:
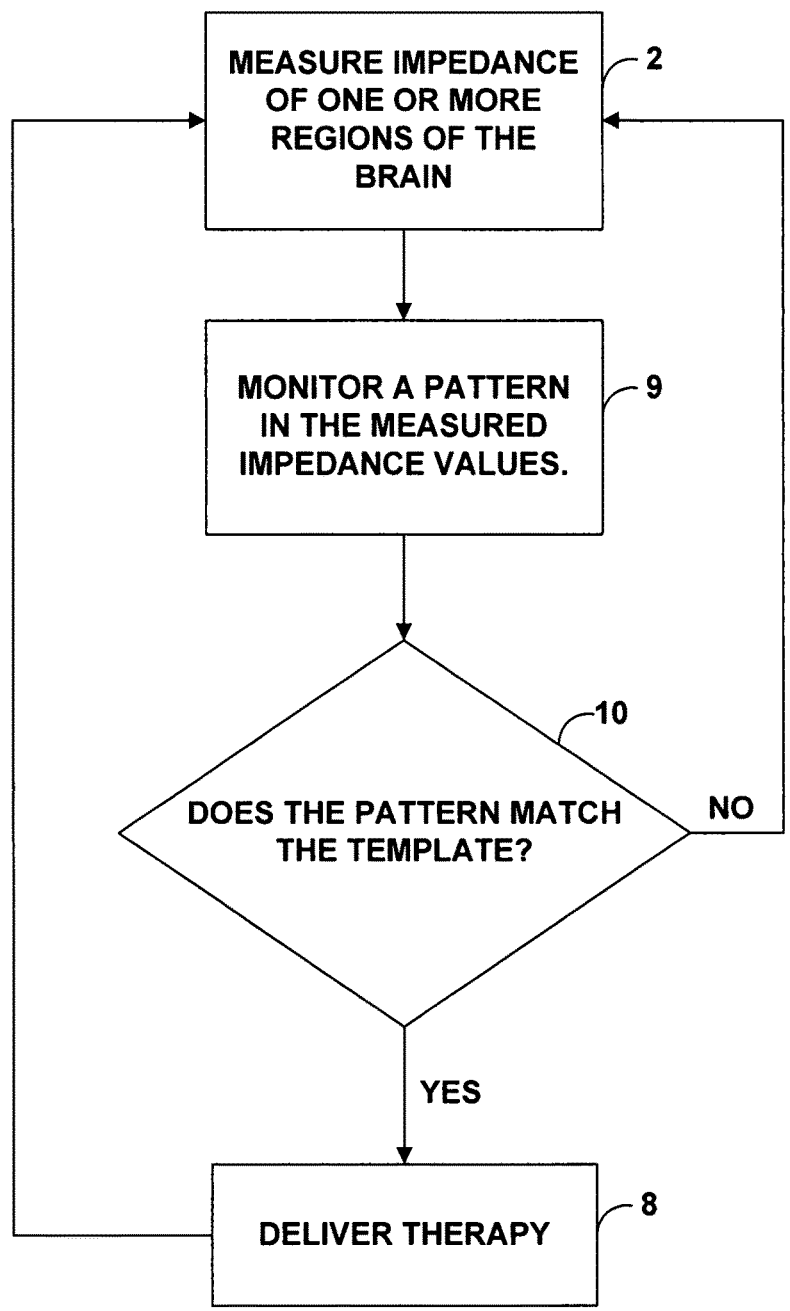
FIG. 1B is a flow diagram illustrating another method for predicting seizure in a patient by measuring an impedance of the brain of the patient and comparing a pattern in the measured impedance to a template.

FIG. 1B is a flow diagram illustrating another embodiment of method for predicting the onset of a seizure in a patient by measuring an impedance of the brain of the patient. The method shown in FIG. 1B is similar to that shown in FIG. 1A, except that rather than comparing the measured impedance to a threshold value (4) and delivering therapy (8) if the measured impedance is greater than or equal to the threshold value (6), the method shown in FIG. 1B involves continuously monitoring a pattern (also referred to as a trend) in the measured impedance values (9). In this way, the method may use signal analysis techniques such as correlation to implement a closed-looped system for responding to the onset of a seizure.

If the pattern of the impedance measurements correlates well, i.e., matches, with a pattern template (10), therapy is delivered to the patient (8). In some embodiments, the template matching algorithm that is employed to determine whether the pattern matches the template (10) may not require a one hundred percent (100%) correlation match, but rather may only match some percentage of the pattern. For example, if the measured impedance values exhibit a pattern that matches about 75% or more of the template, the algorithm may determine that there is a substantial match between the pattern and the template. The pattern template may be generated in a trial phase, an example of which is shown in FIG. 2B and described below. The template may be developed from recording the impedance activity prior to, and possibly during or after, an actual seizure. In one embodiment, a pattern for impedance values that characterize a brain state that will likely lead to a seizure is a rate of change of the impedance measurements over time. For example, a positive increase in the time rate of change (i.e., the slope or first derivative) of the impedance measurements may indicate a likelihood of a seizure, although a decrease (negative slope) in rate of change or another pattern may also be indicative of the likelihood of a seizure. Alternatively, if the time rate of change (i.e., the slope) of the impedance measurements matches or exceeds the time rate of change of the template, therapy may be delivered to the patient (8). The exact trend that is indicative of a brain state in which a seizure is likely may be determined during a trial phase, which is described below with reference to FIG. 2B.

As various examples, the measured impedance signal may be analyzed for slope, amplitude, temporal correlation or frequency correlation with a template signal, or combinations thereof. If the measured impedance signal has a slope that exceeds a threshold, as mentioned above, a positive indication of seizure onset may be indicated. Alternatively, a correlation between inflection points in the amplitude waveform of the impedance signal or other critical points and a template may indicate a likelihood of a seizure onset.

For amplitude correlation, the amplitude of the measured impedance signal may be correlated with a threshold value, as described above. For temporal correlation, the signal may be sampled with a sliding window and compared to a template to identify a signal that correlates well with the template. For example, a processor of the implanted medical device or an external device may perform a correlation analysis by moving a window along a digitized plot of the amplitude of the measured impedance at regular intervals, such as between about one millisecond to about ten millisecond intervals, to define a sample of the impedance signal. The sample window is slid along the plot until a correlation is detected between the waveform of the template and the waveform of the sample of the impedance signal defined by the window. By moving the window at regular time intervals, multiple sample periods are defined. The correlation may be detected by, for example, matching multiple points between the template waveform and the waveform of the plot of the impedance signal over time, or by applying any suitable mathematical correlation algorithm between the sample in the sampling window and a corresponding set of samples stored in the template waveform.

For frequency correlation, the impedance signal may be analyzed in the frequency domain to compare selected frequency components of the impedance signal to corresponding frequency components of the template signal. For example, one or more specific frequency bands may be more revealing than others, and the correlation analysis may include a spectral analysis of the impedance signal component in the revealing frequency bands. The frequency component of the impedance signal may be compared to a frequency component of a template.

In each of the embodiments described above, the one or more templates may be stored within the implanted medical device or an external device, such as a programming device for the implanted medical device. In some embodiments, different templates are employed and selected based on the patient physiological condition, which may be affected by, for example, the time of day or activity (e.g., sleeping, exercising, etc.).

FIG. 2A is a flow diagram illustrating a technique for determining one or more threshold values to compare measured impedance values against in order to determine whether to deliver therapy to a patient. The absolute impedance value that indicates a high probability of seizure may differ depending on the patient. Factors that may affect the threshold value may include factors such as the age, size, and relative health of the patient. The threshold impedance values may even vary for a single patient, depending on fluctuating factors such as the state of hydration, which may affect the fluid levels within the brain of the patient. Accordingly, it may be desirable in some cases to measure the impedance of a particular patient over a finite trial period of time that may be anywhere for less than one week to one or more months in order to tune the trending data or threshold values to a particular patient.

It is also believed that it is possible for the relevant threshold values to be the same for two or more patients. In such a case, one or more previously generated threshold values may be a starting point for a clinician, who may adapt (or "calibrate" or "tune") the threshold values to a particular patient. The previously generated threshold values may be, for example, an average of threshold values for a large number (e.g., hundreds, or even thousands) of patients.

The impedance of a patient's brain is measured during a trial period of time (11). The impedance may be measured substantially continuously or at regular intervals, such as at a frequency of about 1 Hz to about 100 Hz. As previously discussed, the trial period may be anywhere from less than a week to one or more months. The trial period is preferably long enough to measure the impedance of the patient's brain at different hydration levels and during the course of different patient conditions (e.g., sleeping, exercising, eating, and so forth). As previously described, the impedance values may change depending on the fluid loading within the brain of the patient, which is typically not a constant value, as well as other known and/or unknown factors. In addition, it is also desirable for the trial period to span at least one seizure. Two or more seizures may be desirable in order to observe any possible fluctuations in the threshold values.

During the same trial period of time, the actual occurrence of a seizure is sensed and the date and time of the seizure are recorded (12). Any suitable technique may be used for detecting the actual occurrence of a seizure. In one embodiment, a system using known techniques of measuring and analyzing EEG or electrocorticogram (ECoG) waveforms may be used. EEG signals may be recorded via external or implanted electrodes, while ECoG signals, which are deep brain counterparts to EEG signals, typically require the implantation of electrodes on the surface of the brain itself or on the dura matter that surrounds the brain. In other embodiments, a system that detects an abnormal tremor or abnormal body movement, e.g., via one or more accelerometers may be used to detect the actual occurrence of a seizure. In yet another embodiment, a heart rate of the patient may be monitored, where a change in heart rate may indicate an onset of a seizure.

In another embodiment, a patient may provide feedback via a patient programmer or another device to indicate the occurrence of a seizure. The patient may, for example, press a button on a device prior to, during or after the actual occurrence of a seizure to cause the device to record the date and time, or alternatively, cause the medical device that includes the impedance sensing module to record the date and time of the seizure. As yet another alternative, the patient may manually input data relating to the date and time of the seizure into a device after the occurrence of the seizure. Patient feedback prior to the seizure may not be realistic or feasible because the patient typically cannot predict the onset of a seizure.

The impedance measurements are associated with the actual occurrence of a seizure (14) in order to determine the impedance value or values that are indicative of a brain state that may occur prior to the onset of a seizure. In one embodiment, a clinician or computing device may review the data relating to the occurrence of a seizure, and associate one or more impedance measurements with the occurrence of the seizure by matching the date and time of occurrence of the seizure with the impedance measurement that was recorded at substantially the same date and time, or within a certain range of the date and time. For example, the clinician may be interested in determining the impedance of one or more regions of the brain within a particular range of time prior to the onset of the seizure because such a time range may be more relevant to delivering preemptive therapy to prevent the onset of the seizure.

If more than one seizure occurred during the trial period, and the impedance values occurring within a certain time range prior to the onset of the seizure differ for each seizure, the clinician may average the impedance values or may use the lowest impedance value as the threshold value. Using the lowest impedance value is a conservative approach because although not all seizures occurred when the brain or region of the brain exhibited the lowest impedance value, at least one seizure occurred when the brain exhibited the lowest impedance value.

If the impedance was measured in more than one region of the patient's brain, the clinician may use the associated impedance measurements in order to determine which, if any, region exhibited changes in impedance prior to the actual occurrence of the seizure. If more than one region exhibited changes in impedance, the clinician may choose to monitor the region that exhibited the most consistent changes or greatest changes for the chronic impedance sensing and therapy delivery system. Alternatively, the impedance of more than one region of the brain may be monitored on a chronic basis (i.e., after the trial period when a therapy system is implanted in the patient for chronic therapy delivery).

After correlating the impedance measurements with the occurrence of a seizure, the clinician may record the relevant impedance values as the threshold value (16). Alternatively, the correlation and threshold value recording may be automatically performed by a computing device or with the aid of a computing device.

FIG. 2B is a flow diagram illustrating a technique for determining one or more trend templates to which a pattern in measured impedance values may be compared in order to predict a seizure. The technique shown in FIG. 2B is similar that shown in FIG. 2A, except that rather than associating the actual occurrence of a seizure with impedance measurements to determine a threshold value, the impedance measurements are associated with the seizure in order to determine a pattern or trend in the impedance measurements that occurred prior to the onset of the seizure. As with the threshold values, the trend in impedance measurements that indicates a high probability of seizure may differ depending on the patient. It is also believed that it is possible for the relevant trending data to be the same for two or more patients. In such a case, one or more previously generated trend templates may be a starting point for a clinician, who may adapt (or "calibrate" or "tune") the template to a particular patient.

In the technique shown in FIG. 2B, after associating the actual occurrence of a seizure with more than one impedance measurement that was taken prior to the actual occurrence of the seizure (14), a pattern in the impedance values associated with the actual seizure may be determined (16). As previously discussed, the trend may be a rate of change, i.e., slope, of the impedance measurements, which are typically in the form of amplitude measurements, over time or a series of different slopes and transition points in a waveform of the impedance measurements. Thus, the associated impedance values would include the impedance values over a specific range of time prior to and possibly during the actual occurrence of the seizure. In one embodiment, the relevant period of time begins prior to the occurrence of the seizure and ends at the onset of the seizure. A pattern may be determined (16) by any suitable means. In one embodiment, the clinician may plot the impedance values over time and use the slope of the plot as the trend template. The slope of the plot represents the rate of change of the impedance values as a function of time. Alternatively, a computing device may generate the plot. After determining the relevant trend in impedance measurements that indicates the onset of a seizure, the clinician and/or computing device may record the trend in memory of a device and the trend may define a template for determining an onset of a future seizure (18).

In other embodiments, a pattern or trend other than a simple slope of the impedance measurements over time may define the template. For example, the template may include a series of different slopes and transition points in the waveform of the measured impedance.

Figure 3:
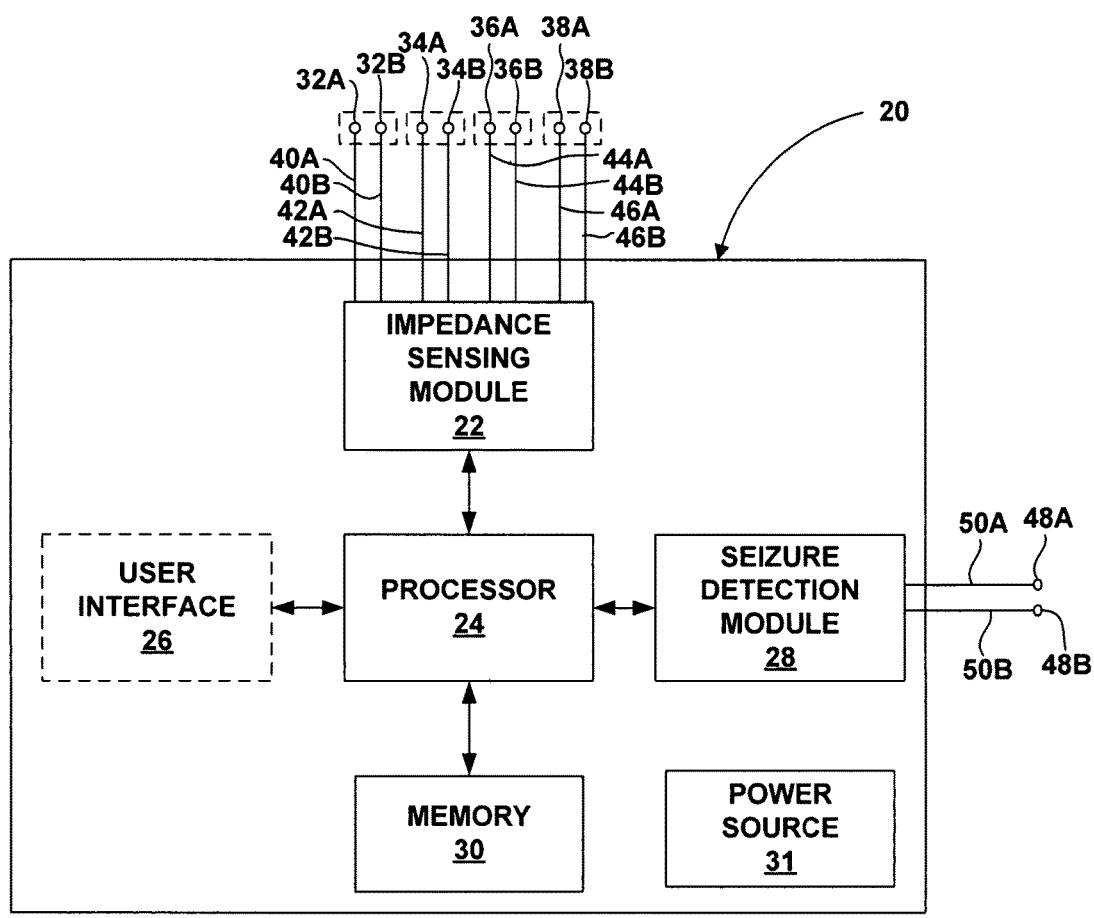
FIG. 3 is a block diagram illustrating a medical device that may be used during a trial stage to determine the threshold impedance values or trend template that indicates a brain is in a state in which a seizure is likely.

FIG. 3 is a block diagram illustrating a medical device 20 that may be used during a first trial (or "learning") stage to determine the threshold impedance values or trend template to use in a system and method for treating seizures. In the example of FIG. 3, medical device 20 includes impedance sensing module 22, processor 24, user interface 26, seizure detection module 28, memory 30, and power source 31. Medical device 20 may be used during a trial phase, e.g., prior to implantation of a chronic therapy delivery system for treating seizures.

Impedance sensing module 22 may include any suitable circuitry for measuring the impedance of the brain of a patient via one or more groups of electrodes 32A-B, 34A-B, 36A-B, and 38A-B that are implanted in different regions of the brain. Electrodes 32A-B, 34A-B, 36A-B, and 38A-B may be implanted to measure the impedance near key regions of the brain, which are regions of the brain that are relevant to the occurrence of seizures. The key regions of the brain may include, for example, regions of the brain to which therapy is delivered in order to treat or prevent seizures. Examples of key regions of the brain include the cortex (e.g., front or motor cortex), brainstem, cranial nerves (e.g., the vagus nerve), or deep brain regions, such as the anterior thalamus, ventrolateral thalamus, globus pallidus, substantia nigra pars reticulata, subthalamic nucleus, neostriatum, cingulated gyrus or the cingulate gyrus. In one embodiment, one or more sets of electrodes 32A-B, 34A-B, 36A-B, and 38A-B may be implanted to measure the impedance across the thalamus or cortex of the brain.

If a particular region of the brain is known to exhibit the most revealing changes in impedance values, the one or more groups of electrodes 32A-B, 34A-B, 36A-B, and 38A-B may be implanted in that region, rather than in different regions of the brain. Phantom lines indicating the grouping of the electrodes are shown in FIG. 3 for purposes of illustration. One example of a suitable impedance sensing circuit that may be included in impedance sensing module 22 is shown in FIGS. 6 and 7 and described below.

Each group of electrodes includes at least two electrodes in order to provide a current across tissue of the patient for the impedance measurement. At least one electrode of the group acts as an anode while the other electrode acts as the cathode. The stimulation current may be relatively low so that the patient does not feel the current. For example, the stimulation current may be in a range of about 500 nA to about 10 μA, although other stimulation currents may be used. Electrodes 32A-B, 34A-B, 36A-B, and 38A-B are electrically coupled to impedance sensing module 22 via conductors within implantable medical leads 40A-B, 42A-B, 44A-B, and 46A-B, respectively. In another embodiment, if medical device 20 is implanted within the patient, the housing of the medical device may be conductive or may include one or more electrodes that may act as an anode or cathode for delivering the impedance measuring stimulation current.

It may be desirable for electrodes 32A-B to be implanted in the patient via a common burr cap hole, electrodes 34A-B to be implanted via a common burr cap hole, and so forth with respect to electrodes 36A-B and 38A-B. In some embodiments, one or more electrodes in each group of electrodes 32A-B, 34A-B, 36A-B, and 38A-B may be disposed on a common housing of a cranial implant. The cranial implant may provide an advantage over leads in that the cranial implant may substantially fix the relative position of each electrode in the group of electrodes 32A-B, 34A-B, 36A-B, and 38A-B. That is, using electrodes 32A-B as an example, when electrodes 32A and 32B are carried by a cranial implant, the cranial implant typically exhibits limited movement, and accordingly, electrodes 32A and 32B exhibit limited movement relative to each other.

Impedance sensing module 22 may provide processor 24 with a signal indicative of the measured impedance. Impedance sensing module 22 provides an impedance measurement by translating the impedance to an output voltage or current. The signal may be sent to processor 24 intermittently or near continuously. If a chopper stabilized instrumentation amplifier, such as the one shown in FIGS. 6 and 7, is incorporated into impedance sensing module 22, the amplifier amplifies and filters the output from electrodes 32A-B, 34A-B, 36A-B, and 38A-B to produce a stable, low noise signal with very low power requirements.

Processor 24 may include a microprocessor, a controller, a digital signal processor (DSP), an application specific integrated circuit (ASIC), a field programmable gate array (FPGA), discrete logic circuitry or the like. In some embodiments, impedance sensing module 22 measures impedance by sending a known current across tissue of the patient, for example, from electrode 32A to electrode 32B, and determining the resulting voltage at electrode 32B. In such embodiments, processor 24 may control the timing of the delivery of the stimulation current across electrodes 32A-B, 34A-B, 36A-B, and/or 38A-B, as well as the amplitude, pulse width, and rate of the stimulation current.

Processor 24 also controls seizure detection module 28. Seizure detection module 28 implements any known methods for detecting the actual occurrence of a seizure. In one embodiment, seizure detection module 28 may include circuitry for measuring brain activity via EEG, which typically measures/monitors electrical activity of the brain by recording the voltage difference between electrodes placed on the scalp. In other embodiments, seizure detection module 28 includes circuitry for measuring brain activity via ECoG data, which typically measures/monitors electrical activity of the brain by recording the voltage difference between electrodes implanted subdurally or in the cerebral cortex of the brain. In the embodiment shown in FIG. 3, electrodes 48A-B are electrically coupled to seizure detection module 28 via leads 50A-B. Electrodes 48A-B may be implanted in some embodiments, and externally placed on the scalp of the patient in other embodiments.

Under the control of processor 24, seizure detection module 28 may obtain EEG data, ECoG data, or other data indicative of seizures via electrodes 48A-B and analyze the EEG, ECoG or other data using known techniques to determine when a seizure occurred. Processor 24 may receive a signal from seizure detection module 28 when an actual seizure occurred. Alternatively, processor 24 may receive EEG data, ECoG data, or other data from seizure detection module 28 and analyze the data to determine when a seizure occurred.

Many existing seizure prediction systems and methods rely on EEG data to determine when a seizure has started. In those existing systems, therapy may be delivered when the EEG data exhibits a certain characteristic. For example, in one seizure predicting procedure discussed in commonly-assigned U.S. Pat. No. 7,006,872, entitled, "CLOSED LOOP NEUROMODULATION FOR SUPPRESSION OF EPILEPTIC ACTIVITY," a seizure is predicted based on whether a sensed EEG starts to show synchrony as opposed to the normal stochastic features. In contrast, the present system and method monitors the impedance of the brain to predict the onset of a seizure before the actual occurrence of the seizure. It is believed that monitoring the impedance of the brain may be useful in predicting seizure before systems and methods monitoring EEG data. The earlier prediction of seizure provides a larger window of opportunity for delivering therapy to the patient to circumvent or preempt the seizure. An earlier detection of the seizure may help prevent delays in therapy delivery.

In addition, processing EEG data may consume more power than processing impedance data, at least with the impedance sensing circuitry shown in FIGS. 6 and 7 and described below. The lower power requirements of the present impedance-based system may help decrease the size of any medical devices incorporating the seizure prediction system as compare to those medical devices incorporating a seizure prediction system based on EEG data. Accordingly, a system relying on impedance to predict seizure may provide an additional advantage of decreasing the size of a medical device into which it is incorporated, which may be particularly beneficial in the case of an implanted medical device.

In an alternate embodiment, in addition to or instead of relying on EEG data, the occurrence of a seizure may be determined based on patient feedback. As described above, the patient may generate a patient marker via a patient programmer to record the date and time of a seizure. The patient marker may be created before, during or after the seizure. Regardless of the timing of the patient marker relative to the onset of the seizure, the patient marker alone should be sufficient data for the clinician or computing device to determine what impedance values are associated with the onset of a seizure.

Other techniques for determining when a seizure occurred may also be used. For example, other embodiments may include detection of abnormal tremor or abnormal body movement or monitoring the heart rate of the patient.

Processor 24 associates the actual occurrence of a seizure with impedance measurements (or signals representing the impedance measurements), and determines at least one threshold impedance value or a trend in impedance measurements that indicates a brain state indicative of a possibility of a seizure, such as a state just prior to the onset of a seizure. Processor 24 may use any of the techniques described above with respect to FIGS. 2A and 2B to find the relevant threshold value(s) or trends. For example, processor 24 may determine the rate of the change of the impedance values as a function of time during a time period beginning before the occurrence of the seizure. As another example, processor 24 may determine a threshold impedance value by associating one or more impedance measurements with the occurrence of the seizure by matching the date and time of occurrence of the seizure with the impedance measurement that was recorded at substantially the same date and time, or within a certain range of the date and time.

In some embodiments, processor 24 does not determine a threshold value or trend, but only stores the associated impedance measurements in memory 30 for later retrieval and analysis by a clinician, who may utilize another computing device to determine the threshold impedance value(s) or the relevant trends in impedance measurements. In addition to or instead of storing the associated impedance measurements, processor 24 may store all of the signals (or actual measured impedance values) from impedance sensing module 22, as well as all of the signals from seizure detection module 28 in memory 30.

Memory 30 of system 20 may include any volatile or non-volatile media, such as a RAM, ROM, NVRAM, EEPROM, flash memory, and the like. Memory 30 may also store program instructions that, when executed by processor 24, cause impedance sensing module 22 to deliver stimulation to measure impedance of the brain and/or cause and seizure detection module 28 to sense seizures. Accordingly, computer-readable media storing instructions may be provided to cause processor 24 to provide functionality as described herein.

Impedance sensing module 22, processor 24, and seizure detection module 28 may be coupled to power source 47. Power source 47 may take the form of a small, rechargeable or non-rechargeable battery, or an inductive power interface that transcutaneously receives inductively coupled energy. In the case of a rechargeable battery, power source 47 similarly may include an inductive power interface for transcutaneous transfer of recharge power.

Medical device 20 may be external to the patient and may utilize external electrodes 32A-B, 34A-B, 36A-B, 38A-B, and 48A-B. Alternatively, electrodes 32A-B, 34A-B, 36A-B, 38A-B may be implanted while electrodes 48A-B for seizure detection module 28 are external to the patient. As yet another alternative, all electrodes 32A-B, 34A-B, 36A-B, 38A-B, and 48A-B may be implanted within the brain of the patient. In embodiments in which medical device 20 includes both internal and external components, impedance sensing module 22, processor 24, user interface 26, seizure detection module 28, memory 30, and/or power source 31 may be separate housings. The housings may be rigid or flexible, and may be fabricated from any suitable biocompatible material, such as titanium or silicone. For example, in embodiments in which electrodes 32A-B, 34A-B, 36A-B, 38A-B, which are electrically coupled to impedance sensing module 22, are implanted within the patient, but electrodes 48A-B, which are electrically coupled to seizure detection module 28, are attached to an external surface of the patient, impedance sensing module 22 may be in a separate housing from the other components of medical device 20. Impedance sensing module 22 may be implanted within the patient and telemetrically coupled to processor 24, which may be in a housing carried externally.

User interface 26 is optional and is thus shown in phantom lines in FIG. 3. In embodiments in which medical device 20 includes an external component, medical device 20 may include user interface 26 is optional. User interface 26 may include a display, input device (e.g., a keyboard, touch screen, buttons, a mouse, etc.) for a clinician to retrieve information from memory 30, program processor 24, and/or otherwise interact with processor 24. Alternatively, the clinician may retrieve information from memory 30 and/or program processor 24 via wired or wireless telemetry.

Figure 4:
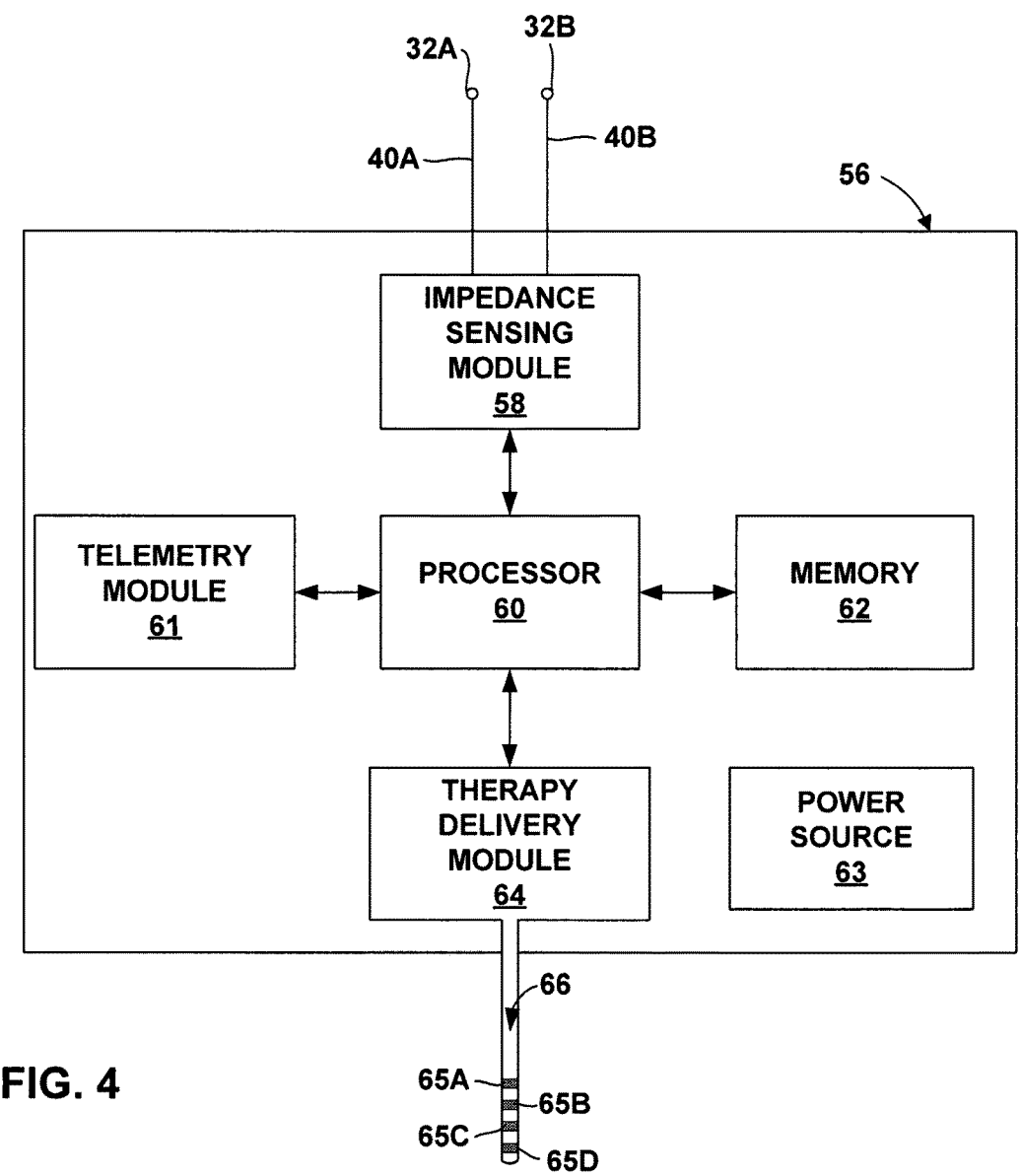
FIG. 4 is a block diagram illustrating an embodiment of an implantable medical device that may be used to predict the onset of a seizure in a patient and deliver electrical stimulation therapy to the patient.

FIG. 4 is a block diagram illustrating an embodiment of an implantable medical device (IMD) 56 that may be used to predict the onset of a seizure in a patient and deliver therapy to prevent the onset of the seizure or to otherwise mitigate the effects of the seizure. In other embodiments, implantable medical device 56 may include both implanted and external portions. Medical device 56 includes impedance sensing circuit 58, processor 60, memory 62, and power source 63, which may be the same as the impedance sensing circuit 22, processor 24, memory 30, and power source 31, respectively, of medical device 20. Medical device 56 also includes telemetry module 61 and therapy delivery module 64.

If medical device 56 includes more than one portion, the different portions may communicate via wired or wireless telemetry. For example, if impedance sensing module 58 is enclosed in a separate housing from processor 60 and therapy delivery module 64, impedance sensing module 58 may provide processor 60 with impedance measurements via wireless telemetry.

As with impedance sensing module 22 of medical device 20, impedance sensing module 58 may measure the impedance of the brain via electrodes 32A-B, which are coupled to impedance sensing circuit 58 via leads 40A-B. A relatively low stimulation current may be delivered across a region of the brain via electrodes 32A-B. For example, the stimulation current may be in a range of about 500 nA to about 10 µA, although other stimulation currents may be used. If desired, multiple sets of electrodes may be used to sense the impedance in the same region of the brain or in multiple regions of the brain. By placing electrodes in more than one region in the patient's brain, the impedance at more than one region may be monitored. The impedance may be more revealing in one brain region than in other regions. In some embodiments, the housing of medical device 56 may include one or more electrodes for delivering stimulation current to measure impedance and/or at least a part of the housing of medical device 56 may be conductive act as an electrode. In those embodiments, impedance may be sensed via two or more electrodes on the housing of medical device 56 or via at least one electrode on the housing of medical device 56 and at least one of electrodes 32A-B. Other sensing electrode arrangements may also be used.

Impedance sensing circuitry associated with sensing electrodes 32A-B is provided within impedance sensing module 58. In general, impedance sensing module 58 provides a measurement of an impedance of the brain by translating the sensed impedance to an output voltage or current. The output of impedance sensing module 58 may be received by processor 60. Processor 60 may apply additional processing, e.g., convert the output to digital values for processing. In some embodiments, processor 60 stores the values in memory 62, and/or transmits the values to an external programmer via telemetry module 61. processor 60 may also control the timing of the delivery of the stimulation current via electrodes 32A-B for measuring impedance.

Processor 60 also controls the delivery of therapy to the patient based on the output of impedance sensing module 58. In one embodiment, processor 60 analyzes the measured impedance to determine whether the brain of the patient (i.e., one or more regions within the brain) is in a state indicative of a possibility of a seizure. If processor 60 determines the brain is the state indicative of a possibility of a seizure, processor 60 may generate a seizure indication. The seizure indication may be a value, flag, or signal that is stored or transmitted to indicate determination of a seizure. Therapy delivery module 64 or processor 60 may take action in response to the seizure indication. The generation of the seizure indication may cause, for example, therapy delivery module 64 to deliver therapy to the patient or cause processor 60 to generate an alarm or other notification that indicates the possibility that a seizure may occur. In some embodiments, processor 60 may record the seizure indication in memory 62 for retrieval and further analysis by a clinician. For example, seizure indications may be recorded over time, e.g., in a loop recorder, and may be accompanied by impedance values associated with the seizure indications. In general, the generation of the seizure indication may cause processor 60 to take some action or instruct another module 58, 61 or 64 to take some action. Alternatively, impedance sensing module 58 or another module within medical device 56, an external programming device, or another type of external computing device may include a processor that processes the impedance measurements and generates one or more seizure indications when the impedance measurements indicate the brain in the state that is indicative of a possibility of a seizure.

As other examples, processor 60 may receive the impedance measurements from impedance sensing circuit 58 and compare the measured impedance to one or more threshold values that were determined during a first stage of the therapy program using, for example, medical device 20 shown in FIG. 3. For example, in one embodiment, when the measured impedance value is greater than or equal to the threshold value, processor 60 may control therapy delivery module 64 to deliver electrical stimulation therapy to the patient via electrodes 65A-D of lead 66. Alternatively, therapy delivery module 64 may deliver stimulation therapy via one or more electrodes on a housing of medical device 56. For example, electrical stimulation may be delivered via two or more electrodes on the housing of medical device 56 or via at least one electrode on the housing (or a conductive housing itself) of medical device 56 and at least one of electrodes 65A-B. Other stimulation electrode arrangements may also be used.

As another example, processor 60 may receive the impedance measurements from impedance sensing circuit 58 and compare the trend of the impedance measurements to one or more trend templates. Processor 60 may implement an algorithm that recognizes a trend of impedance measurements that characterize a brain state that is predictive of the onset of a seizure. If the trend of the impedance measurements matches or substantially matches the trend template, processor 60 controls therapy delivery module 64 to deliver electrical stimulation to the patient via electrodes 65A-D of lead 66 or via at least one electrode on the housing of medical device 56 or a conductive housing of medical device 56. As previously described, instead of or in addition to delivering therapy in response to measured impedance measurements that substantially match the trend template, a patient alarm may be activated, processor 60 may record the date and time of the impedance measurements and/or the actual impedance measurements for future analysis by a clinician, a signal may be transmitted to another device (e.g., an external programming device) that records the date and time of the impedance measurements, and so forth.

In some embodiments, the electrical stimulation therapy is delivered to regions of the brain that are directly related to seizures. For example, electrical stimulation may be delivered to the thalamus or the cortex of the brain. Electrodes 65A-D are electrically coupled to therapy delivery module 64 via conductors within lead 66. In one embodiment, an implantable signal generator or other stimulation circuitry within therapy delivery module 64 delivers electrical signals (e.g., pulses or substantially continuous-time signals, such as sinusoidal signals) to a target stimulation site within the brain via at least some of electrodes 64 under the control of a processor 60. The signals may be delivered from therapy delivery module 64 to electrodes 65A-D via a switch matrix and conductors carried by lead 66 and electrically coupled to respective electrodes 65A-D. The implantable signal generator within therapy delivery module 64 may be coupled to power source 63.

The exact parameters of the stimulation therapy, such as the amplitude or magnitude of the stimulation signals, the duration of each stimulus, the waveform of the stimuli (e.g., rectangular, sinusoidal or ramped signals), may be specific for the particular target stimulation site (e.g., the region of the brain) involved as well as the particular patient. In the case of stimulation pulses, the stimulation therapy may be characterized by selected pulse parameters, such as pulse amplitude, pulse rate, and pulse width. In addition, if different electrodes are available for delivery of stimulation, the therapy may be further characterized by different electrode combinations. Known techniques for determining the optimal stimulation parameters may be employed. In one embodiment, electrodes 65A-D are implanted to deliver stimulation therapy to an anterior nucleus of the thalamus of the brain of the patient, and stimulation therapy is delivered via a select combination of electrodes 65A-D to the anterior nucleus with electrical stimulation including a frequency of 120 Hz, a voltage of about 4 volts, and a pulse width of about 100 microseconds. However, other embodiments may implement stimulation therapy including other stimulation parameters.

In the embodiment of FIG. 4, lead 66 is substantially cylindrical. In other embodiments, lead 66 may be paddle-shaped (i.e., a "paddle" lead). Electrodes 65A-D may be ring electrodes, segmented or partial ring electrodes. The configuration, type, and number of electrodes 65A-D and leads 66 illustrated in FIG. 4 are merely exemplary. In other embodiments, two or more leads 66 may be coupled either directly or indirectly (e.g., via a lead extension) to therapy delivery module 64 of medical device 56.

Processor 60 also controls telemetry module 61 to exchange information with an external programmer, such as a clinician programmer and/or patient programmer by wired or wireless telemetry. Processor 60 may control telemetry module 61 to communicate with the external programmer on a continuous basis, at periodic intervals, or upon request from the programmer. Telemetry module 61 may operate as a transceiver that receives telemetry signals from an external programmer and transmits telemetry signals to an external programmer. Telemetry module 61 may also include a transmitter to transmit signals from IMD 56 to an external programmer or to another IMD or external medical device.

In some embodiments, telemetry module 61 may include a chopper stabilized instrumentation amplifier, such as one shown in FIGS. 6 and 7. More specifically, the receiver portion of telemetry module 61 may include the back end of a chopper stabilized instrumentation amplifier, referred to as a chopper stabilized mixer amplifier and feedback path, which produces a baseband signal from a received telemetry signal. The receiver portion is described in this disclosure as including only the back end (chopper stabilized mixer amplifier) because the corresponding front end is located in the transmitter portion of an external programmer or another device in communication with medical device 56.

The receiver portion may also include a clock synchronizer that includes another chopper stabilized mixer amplifier, e.g., as further described in commonly-assigned U.S. patent application Ser. No. 11/700,404, entitled, "CHOPPER-STABILIZED INSTRUMENTATION AMPLIFIER," to Timothy J. Denison and filed on Jan. 31, 2007, U.S. patent application Ser. No. 11/700,738, entitled, "CHOPPER-STABILIZED INSTRUMENTATION AMPLIFIER FOR WIRELESS TELEMETRY," to Timothy J. Denison and filed on Jan. 31, 2007, and U.S. patent application Ser. No. 11/700,405, entitled, "CHOPPER-STABILIZED INSTRUMENTATION AMPLIFIER FOR IMPEDANCE MEASUREMENT," to Timothy J. Denison and filed on Jan. 31, 2007, the entire content of each of which is incorporated herein by reference. A chopper stabilized mixer amplifier as described in the aforementioned patent applications can produce an output that can be used by a phase lock loop to generate a correction signal that is used to synchronize the receiver portion of telemetry module 61 with the transmitter of the external programmer. The transmitter may include a front end of a chopper-stabilized instrumentation amplifier in the sense that it may include a first chopper stage that modulates an input signal with a radio frequency (RF) for transmission to an external programmer or another implanted or external medical device.

Figure 5:
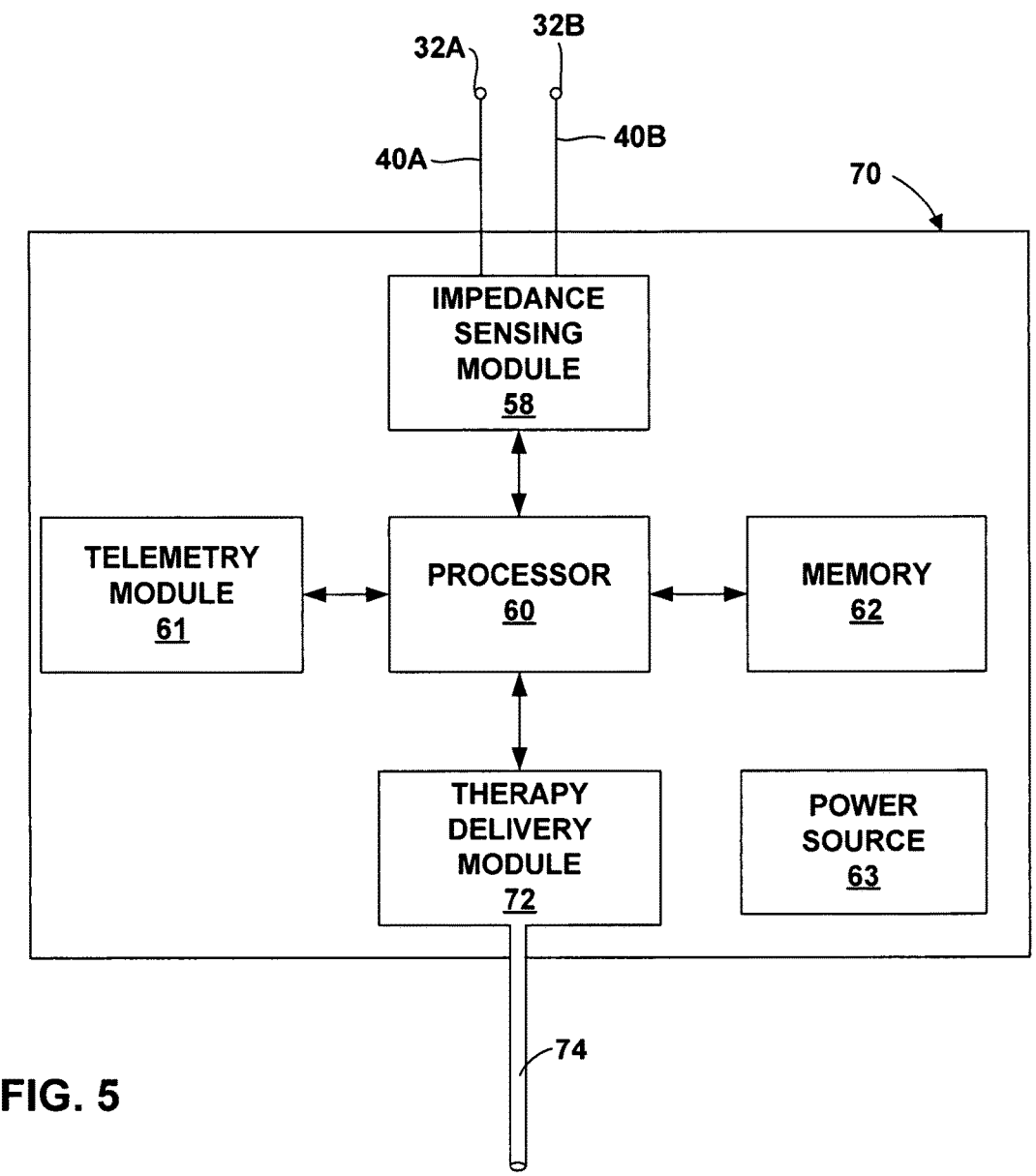
FIG. 5 is block diagram of another embodiment of a medical device that may be used to predict the onset of a seizure in a patient and deliver drug therapy to the patient.

FIG. 5 is block diagram of another embodiment of an implantable medical device 70, which is similar to medical device 56 of FIG. 4. Unlike therapy delivery module 64 of FIG. 4, which delivers electrical stimulation therapy to a patient via lead 66, therapy delivery module 72 of FIG. 5 is configured to deliver a pharmaceutical agent to a patient via catheter 74 upon the prediction of a seizure. Catheter 74 may be any suitable fluid delivery conduit, and therapy delivery module 72 may be any suitable fluid delivery device, such as a drug pump. Upon detecting the onset of a seizure via impedance values measured by impedance sensing circuit 60, processor 60 may control therapy delivery module 72 to deliver a bolus of a drug to the patient. The drug may be delivered directly to target tissue sites within the brain to mitigate the effects of a seizure or to prevent the onset of a seizure. Examples of suitable pharmaceutical agents for treating seizures include, but are not limited to, sodium valproate, benzodiazepine, barbiturates (e.g., Phenobarbital/primidone), ethosuximide, gabapentin, phenytoin, and carbamazepine.

FIG. 6 is a block diagram illustrating an embodiment of a chopper stabilized instrumentation amplifier 80, which may be incorporated into a medical device, for measuring the impedance of one or more regions of the brain of a patient. Instrumentation amplifier 80 may be included in impedance sensing modules 22 and 58 of medical devices 20 (FIG. 3) and 56 (FIG. 4), respectively. An instrumentation amplifier configured for impedance measurement and suitable for use as instrumentation amplifier 80 is described in further detail in the aforementioned, commonly-assigned U.S. patent application Ser. No. 11/700,404, entitled, "CHOPPER-STABILIZED INSTRUMENTATION AMPLIFIER," to Timothy J. Denison. Instrumentation amplifier 80 is configured to achieve stable measurement of impedance values of a brain of a patient at low frequency with very low power.

An impedance sensing module incorporating instrumentation amplifier 80 is alternating current (AC) coupled, which minimizes the possibility of stimulating tissue when delivering an impedance-measuring stimulation current to the tissue within the brain. In general, it is desirable to avoid inadvertently stimulating tissue with the stimulation current used for measuring impedance in order to prevent the patient from feeling the stimulation current (which differs from the stimulation current delivered for therapy delivery), and in order to inadvertently cause muscle or nerve stimulation. In addition, the AC coupling of the impedance sensing module helps prevent corrosion to the electrodes used to measure impedance (e.g., electrodes 32A-B of FIGS. 3 and 4).

Instrumentation amplifier 80 uses a differential architecture and a mixer amplifier to substantially eliminate 1/f noise, popcorn noise, and offset. Dynamic limitations, i.e., glitching, that result from chopper stabilization at low power are eliminated through a combination of chopping at low impedance nodes within a mixer amplifier 84 and feedback via feedback path 86. The signal path of the instrumentation amplifier operates as a continuous time system, providing minimal aliasing of noise or external signals entering the signal pathway at the chop frequency or its harmonics. As a result, instrumentation amplifier 80 can provide stable measurements for low frequency signals, such as physiological signals and other signals having a frequency of less than approximately 100 hertz (Hz), and preferably less than or equal to approximately 2.0 Hz, and more preferably less than or equal to approximately 1.0 Hz, while operating under the constraints of a micro power system, e.g., drawing a supply current of less than or equal to approximately 2.0 microamps, and more preferably less than or equal to approximately 1.0 microamps, and requiring a supply voltage of less than or equal to approximately 2.0 volts, and more preferably less than or equal to approximately 1.5 volts.

As shown in FIG. 6, instrumentation amplifier 80 includes front end 82, mixer amplifier 84, and feedback path 86. In the example of FIG. 6, front end 82 may provide a switched or static capacitive differential interface to mixer amplifier 84, e.g., for measurement of a low frequency voltage amplitude. Front end 82 is configured for impedance measurement. Front end 82 couples a differential modulated (chopped) input signal that carries a low frequency signal of interest on a carrier (chopper) frequency. In other words, front end 82 shifts a low frequency signal that is subject to introduction of low frequency noise by mixer amplifier 84 to a carrier frequency at which the mixer amplifier 84 does not introduce substantial noise into the signal. The low frequency signal of interest may have, for example, a frequency within a range of approximately 0 Hz to approximately 100 Hz. In some embodiments, the carrier (chopper) frequency may be within a frequency range of approximately 4 kHz to 100 kHz. Front end 82 modulates the low frequency signal prior to introduction to mixer amplifier 84 so that the original baseband (low frequency) signal components are not corrupted by noise components introduced by mixer amplifier 84 at low frequency.

Noise generally enters the signal path of instrumentation amplifier 80 through mixer amplifier 84. However, mixer amplifier 84 should not introduce noise to the modulated signal at the carrier frequency. Rather, the noise components are typically present at low frequency and may include 1/f noise or popcorn noise. In addition, noise in the form of dc offset cannot be introduced at the carrier frequency. Mixer amplifier 84 receives and amplifies the up-modulated input signal from front end 82. Again, the up-modulated input signal is up-modulated to the chopper frequency to protect the input signal from low frequency noise and offset.

Mixer amplifier 84 demodulates the modulated input signal from the carrier frequency to the baseband of interest while upmodulating the mixer amp 1/f noise and offset out of the measurement band. Thus, the original low frequency signal components are demodulated back to baseband without the low frequency noise and offset components of the mixer amplifier 84. Mixer amplifier 84 passes only the baseband signals, i.e., signals with frequency components of approximately 100 Hz or less, as output and substantially reduces or eliminates the noise components located at the carrier frequency. Thus, the output of instrumentation amplifier 80 contains the low frequency signal components of interest. In addition, mixer amplifier 84 provides a gain amplifier that amplifies the input signal. In this way, instrumentation amplifier 80 provides a low noise output while operating at low power.

Instrumentation amplifier 80 operates under the constraints of a micro power system and therefore has limited bandwidth. The limited bandwidth of instrumentation amplifier 80 can cause glitching or ripple in the passband of the output signal. As will be described, mixer amplifier 84 may have a modified folded cascode architecture that provides switching, e.g., via CMOS switches, at low impedance nodes. Switching at low impedance nodes enables chopping at higher frequencies where the only limitation would be the charge injection residual offset.

Feedback path 86 is coupled between the output of mixer amp 84 and front end 82 to reduce the ripple. Feedback path 86 may have a differential configuration that substantially eliminates glitching in the output signal by driving the net input signal to mixer amplifier 84 toward zero. In this way, feedback path 86 keeps the signal change at the input of mixer amplifier 84 relatively small in steady state. As a result, instrumentation amplifier 80 achieves a stable, low noise, low distortion output while operating at low power.

An impedance sensing module of a medical device may include multiple instrumentation amplifiers 80. For example, multiple instrumentation amplifiers 80 may be provided in parallel to provide multiple sensing channels. The multiple sensing channels may sense impedance, e.g., at different positions or angles, or via different electrodes. In addition, multiple sensing channels may sense different types of physiological information in addition to impedance, such as electrocardiogram (ECG), electroencephalogram (EEG), electromyogram (EMG), pressure, motion, and the like.

Front end 82 of instrumentation amplifier 80 includes an impedance sensor. In particular, instrumentation amplifier 80 may form a biological impedance sensing device for measuring the impedance of tissue of a brain of a patient. In this way, instrumentation amplifier 80 may be incorporated into a system for detecting seizures and delivering therapy to prevent or otherwise treat the seizure, as described in this disclosure. The impedance sensor formed by front end 82 produces an AC modulated signal that is AC coupled to mixer amplifier 84 through the tissue of the patient. In this case, front end 82 modulates stimulation current to modulate the amplitude of a tissue voltage signal, thereby chopping the impedance signal produced by application of the stimulation current source to the patient brain tissue. Thus, the patient is not exposed to a direct current (DC) signal. Moreover, the modulated signal may not substantially excite the tissue, thereby decreasing the likelihood that the patient may experience discomfort or other detrimental effects from the modulated signal.

According to another example embodiment, front end 82 of amplifier 80 may comprise a continuous time switched capacitor network. The switched capacitor network includes a differential set of switched input capacitors that toggle between input voltages at the positive and negative terminals of instrumentation amplifier 80. By toggling the switched input capacitors at the chopper frequency, the differential input signal is chopped. In this manner, the differential input signal is up-modulated to the carrier frequency, yielding a modulated signal at the differential input of mixer amplifier 84. Accordingly, the inputs to front end 82 may be from electrodes positioned to measure the impedance of a tissue site within the brain.

According to an additional example embodiment, feedback 86 may include a second feedback path (not shown in FIG. 6) in addition to the previously described negative feedback path that reduces glitching in the output of instrumentation amplifier 80 and provides the nominal gain for amplifier 80. This second feedback path provides negative feedback to allow for the construction of a high pass filter. The second feedback path is dominant at low frequencies, i.e., frequencies lower than the cutoff frequency, and the chopper stabilized negative feedback path is dominant at passband frequencies. The high pass filter may have a cutoff frequency approximately equal to, e.g., approximately 2.5 Hz, or 0.5 Hz, or 0.05 Hz. In this case, the first feedback path, i.e., the "chopper stabilizing" feedback path that eliminates glitching at the output, is dominant at pass band frequencies and the second "high-pass filter" feedback path is dominant at low frequencies. The corner frequency of the high pass filter in the second feedback path can be set by the scaling of feedback capacitors in the first feedback path and the time-constant of a switched capacitor integrator in the second feedback path. As one example, the high pass filter provided by this feedback path may be useful for filtering out electrode offsets. The second feedback path may include a high-pass integrator that is chopper stabilized for the lowest 1/f noise floor.

According to yet another embodiment, feedback 86 may include a third feedback path in addition to the first feedback path (not shown in FIG. 6). The third feedback path provides positive feedback to increase the input impedance of instrumentation amplifier 80. The increased input impedance is achieved by sampling the output of instrumentation amplifier 80 and applying a scaled charge to the input of the switched capacitors in front end 82 to provide compensatory charge at the sensor input. The scaled charge may be applied at a point in the signal flow prior to chopping of the input signal. The injected current effectively "replaces" charge lost during the sampling of input chopper capacitors in front end 82. This charge replacement feedback may be considered similar to base current compensation. The positive feedback may increase the equivalent low-frequency input impedance of instrumentation amplifier 80 by an order of magnitude or more. This third feedback path may not be necessary in various applications. If increased input impedance is desired, however, this third feedback path can be readily added.

According to a further example embodiment, instrumentation amplifier 80 may include the previously described second and third feedback paths in addition to the first (chopper stabilizing) feedback path. In this case, the third feedback path does not tap off of the output signal of instrumentation amplifier 80 as previously described. Rather, the third, positive feedback path may tap off of an integrated signal provided by the second, high-pass filter feedback path. Accordingly, various combinations of first, second, and/or third feedback paths may be provided to address glitching, low frequency rejection, and/or amplifier input impedance. In each case, however, instrumentation amplifier 80 includes a front end 82 configured to apply a stimulation current for impedance measurement in combination with means for chopping the stimulation current to produce a chopped impedance signal for application to mixer amplifier 84.

Instrumentation amplifier 80 can provide one or more advantages in a variety of embodiments. For example, as previously described, instrumentation amplifier 80 can achieve stable measurements at low frequency with low power. This is a result of the basic architecture of instrumentation amplifier 80. As another advantage, on-chip, poly-poly capacitors may be used to implement feedback capacitors in instrumentation amplifier 80. Poly-poly capacitors enable fast switching dynamics and can be formed on-chip with other amplifier components. A poly-poly capacitor may be formed on chip with other devices by combining two polysilicon electrodes and an intervening silicon dioxide dielectric. The gain of the instrumentation amplifier can be set by the ratio of the feedback capacitors to the input capacitors and centered around a selected reference voltage. Further, by modulating the input signal at front end 82, the common mode input voltage can swing from rail to rail and mixer amplifier 84 is still able to extract a differential voltage. These advantages are merely exemplary and should be considered a subset of potential advantages provided by instrumentation amplifier 80. Additional advantages are discussed in this disclosure or may occur to those skilled in the art upon consideration of this disclosure. Moreover, such advantages may not coexist in every embodiment.

FIG. 7 is a block diagram illustrating a signal path flow of one embodiment of instrumentation amplifier 80 that may be incorporated into impedance sensing modules 22 (FIG. 3) or 58 (FIG. 4). In general, a known stimulation current 102 is introduced across at least two electrodes positioned in the brain, and mixer amplifier 84 measures the resulting voltage. Based on the known stimulation current ISTIM and resulting voltage, instrumentation amplifier 80 may determine the impedance across the two electrodes, and accordingly, the impedance of the selected brain tissue.

In FIG. 7, front end 82 includes modulator 90 for modulating a low frequency input signal 102 to produce modulated input signal 91. Modulator 90 chops the input signal 102, providing a chopped stimulation current for application across a tissue load. An input capacitance (Cin) 83 couples the output of modulator 90 to summing node 92. For a differential input signal, Cin 83 may include a first input capacitor coupled to a first input of mixer amplifier 84 and a second input capacitor coupled to a second input of mixer amplifier 84. Modulator 90 modulates a differential amplitude of input signal 102 to a carrier frequency provided by clock signal 91A. Clock signal 91A, like other clock signals described in this disclosure, may be a square wave signal that effectively multiplies the signal by plus 1 and minus 1 at a desired clock frequency. In this manner, module 90 chops the input signal 102 prior to application of the input signal to the tissue load and mixer amp 84. Modulator 90 may, in some embodiments, comprise a pair of complementary metal oxide semiconductor (CMOS) single pole, double throw (SPDT) switches that are driven by clock signal 91A to modulate (chop) input signal 102 to the carrier frequency. The CMOS SPDT switches may be cross-coupled to each other to reject common mode signals.

In one example embodiment, the CMOS switches may be coupled to a set of differential capacitors to form a continuous time switched capacitor network that forms input capacitance Cin at the input of mixer amplifier 84. In another example embodiment, the CMOS switches may be coupled to capacitors that AC couple modulated input signal 102 to the input of mixer amplifier 84. In this case, front end 82 is an impedance sensor that modulates a stimulation current that is applied across tissue of a patient.

Feedback summing node 92 will be described below in conjunction with feedback path 86. Summing node 94 represents the introduction of offset and 1/f noise within mixer amplifier 84. At summing node 94, the original baseband components of input signal 102 are located at the carrier frequency. The baseband signal components of input signal 102 may have a frequency within a range of approximately 0 Hz to approximately 100 Hz and the carrier frequency may be approximately 4 kHz to approximately 10 kHz. Noise 93 enters the signal pathway at summing node 94 to produce noisy modulated input signal 95. Noise 93 may include 1/f noise, popcorn noise, offset, and any other external signals that may enter the signal pathway at low (baseband) frequency. At node 94, however, the original low frequency components have already been chopped to a higher frequency band by modulator 90. Thus, the low frequency noise 93 is segregated from the original low frequency components.

Mixer amplifier 84 receives noisy modulated input signal 95 from node 94. In the example of FIG. 7, mixer amplifier 84 includes gain amplifier 96, modulator 98, and integrator 100. Amplifier 96 amplifies noisy modulated input signal 95 to produce amplified signal 97. Modulator 98 demodulates amplified signal 97. That is, modulator 98 modulates noise 93 up to the carrier frequency and demodulates the original baseband signal components from the carrier frequency back to baseband. Modulator 98 may comprise switches, e.g., CMOS SPDT switches, located at low impedance nodes within a folded-cascode architecture of mixer amplifier 84. Modulator 98 is supplied with clock signal 91B to demodulate amplified signal 97 at the same carrier frequency as clock signal 91A. Hence, clock signals 91A, 91B should be synchronous with each other. In some embodiments, clock signal 91A and clock signal 91B may be the same signal, i.e., supplied by the same clock. In other embodiments, e.g., for measurement of reactance, the relative phasing of clock signals 91A, 91B and 91C may be altered.

Integrator 100 operates on demodulated signal 99 to pass the low frequency signal components at baseband and substantially eliminate noise components 93 at the carrier frequency. In this manner, integrator 100 provides compensation and filtering. In other embodiments, compensation and filtering may be provided by other circuitry. However, the use of integrator 100 as described in this disclosure may be desirable. Feedback path 86, as shown in FIG. 7, provides negative feedback to the input of mixer amp 84 to reduce glitching in output signal 101. In particular, feedback path 86 drives modulated signal 95 toward zero in steady state. In this way, feedback 86 keeps the signal change at the input to mixer amplifier 84 small. Feedback path 86 includes a modulator 104, which modulates output signal 101 to produce a differential feedback signal 105 that is added to the signal path between front end 82 and mixer amplifier 84 at node 92.

Feedback path 86 provides capacitor scaling versus the input capacitance Cin of mixer amplifier 84 to produce attenuation and thereby generate gain at the output of amplifier 80. Accordingly, feedback path 86 may include a feedback capacitance (Cfb) 87 that is selected to produce desired gain, given the value of the input capacitance (Cin) 83 of mixer amplifier 84. Integrator 100 may be designed to provide a stable feedback path 86 with acceptable bandwidth while also filtering out the upmodulated offset and 1/f noise from the measurement band.

Clock signal 91C drives modulator 104 in feedback path 86 to modulate output signal 101 at the carrier frequency. Clock signal 91C may be derived from the same clock as clock signal 91B. However, because output signal 101 is single ended, feedback 86 includes two feedback paths that apply the negative feedback to the positive and negative input terminals of mixer amplifier 84. Thus, the two feedback paths should be 180 degrees out of phase with each other, with one of the feedback paths modulating synchronously with modulator 98. This ensures that a negative feedback path exists during each half of the clock cycle.

As an alternative, in some embodiments, mixer amplifier 84 may be configured to generate a differential output signal, rather than a single-ended output signal. A differential output signal may provide positive and negative outputs. In this case, feedback path 86 can feed back the positive output to the positive input of mixer amplifier 84 and feed back the negative output to the negative input of the mixer amplifier. For a differential output signal, feedback path 86 would modulate each of the positive and negative outputs. However, the positive and negative outputs could be modulated in-phase, rather than out of phase. Although a differential output is possible, a feedback path 86 configured to convert a single-ended output to differential feedback will be described herein for purposes of illustration.

In FIG. 7, only the previously described negative feedback path 86 is shown. That is, the previously described feedback paths for increasing input impedance and constructing a high pass filter are excluded from FIG. 7. These feedback paths are excluded in FIG. 7 because they are not necessary for proper operation of instrumentation amplifier 80. However, the feedback paths may be included in other applications.

FIG. 8 is a circuit diagram illustrating an example embodiment of mixer amplifier 84 of instrumentation amplifier 80 in greater detail. As previously described, mixer amplifier 84 amplifies noisy modulated input signal 95 to produce an amplified signal and demodulates the amplified signal. Mixer amplifier 84 also substantially eliminates noise from the demodulated signal to generate output signal 101. In the example of FIG. 8, mixer amplifier 84 is a modified folded-cascode amplifier with switching at low impedance nodes. The modified folded-cascode architecture allows the currents to be partitioned to maximize noise efficiency. In general, the folded cascode architecture is modified in FIG. 8 by adding two sets of switches. One set of switches is illustrated in FIG. 8 as switches 106A and 106B (collectively referred to as "switches 106") and the other set of switches includes switches 108A and 108B (collectively referred to as "switches 108").

Switches 106 are driven by chop logic to support the chopping of the amplified signal for demodulation at the chop frequency. In particular, switches 106 demodulate the amplified signal and modulate front-end offsets and 1/f noise. Switches 106 are embedded within a self-biased cascode mirror formed by transistors M6, M7, M8 and M9, and are driven by chop logic to up-modulate the low frequency errors from transistors M8 and M9. Low frequency errors in transistors M6 and M7 are attenuated by source degeneration from transistors M8 and M9. The output 101 of amplifier 96 is at baseband, allowing an integrator formed by transistor M10 and capacitor 110 (Ccomp) to stabilize feedback path 86 (not shown in FIG. 8) and filter modulated offsets.

Mixer amplifier 84 has three main blocks: a transconductor, a demodulator, and an integrator. The core is similar to a folded cascode. In the transconductor section, transistor M5 is a current source for the differential pair of input transistors M1 and M2. In some embodiments, transistor M5 may pass approximately 800 nA, which is split between transistors M1 and M2, e.g., 400 nA each. Transistors M1 and M2 are the inputs to amplifier 84. Small voltage differences steer differential current into the drains of transistors M1 and M2 in a typical differential pair way. Transistors M3 and M4 serve as low side current sinks, and may each sink roughly 500 nA, which is a fixed, generally nonvarying current. Transistors M1, M2, M3, M4 and M5 together form a differential transconductor.

In this example, approximately 100 nA of current is pulled through each leg of the demodulator section. The AC current at the chop frequency from transistors M1 and M2 also flows through the legs of the demodulator. Switches 106 alternate the current back and forth between the legs of the demodulator to demodulate the measurement signal back to baseband, while the offsets from the transconductor are up-modulated to the chopper frequency. As discussed previously, transistors M6, M7, M8 and M9 form a self-biased cascode mirror, and make the signal single-ended before passing into the output integrator formed by transistor M10 and capacitor 110 (Ccomp). Switches 106 placed within the cascode (M6-M9) upmodulate the low frequency errors from transistors M8 and M9, while the low frequency errors of transistor M6 and transistor M7 are suppressed by the source degeneration they see from transistors M8 and M9. Source degeneration also keeps errors from Bias N2 transistors 66 suppressed. Bias N2 transistors M12 and M13 form a common gate amplifier that presents a low impedance to the chopper switching and passes the signal current to transistors M6 and M7 with immunity to the voltage on the drains.

The output DC signal current and the upmodulated error current pass to the integrator, which is formed by transistor M1, capacitor 110, and the bottom NFET current source transistor M11. Again, this integrator serves to both stabilize the feedback path and filter out the upmodulated error sources. The bias for transistor M10 may be approximately 100 nA, and is scaled compared to transistor M8. The bias for lowside NFET M11 may also be approximately 100 nA (sink). As a result, the integrator is balanced with no signal. If more current drive is desired, current in the integration tail can be increased appropriately using standard integrate circuit design techniques. Various transistors in the example of FIG. 6 may be field effect transistors (FETs), and more particularly CMOS transistors.

Figure 9:
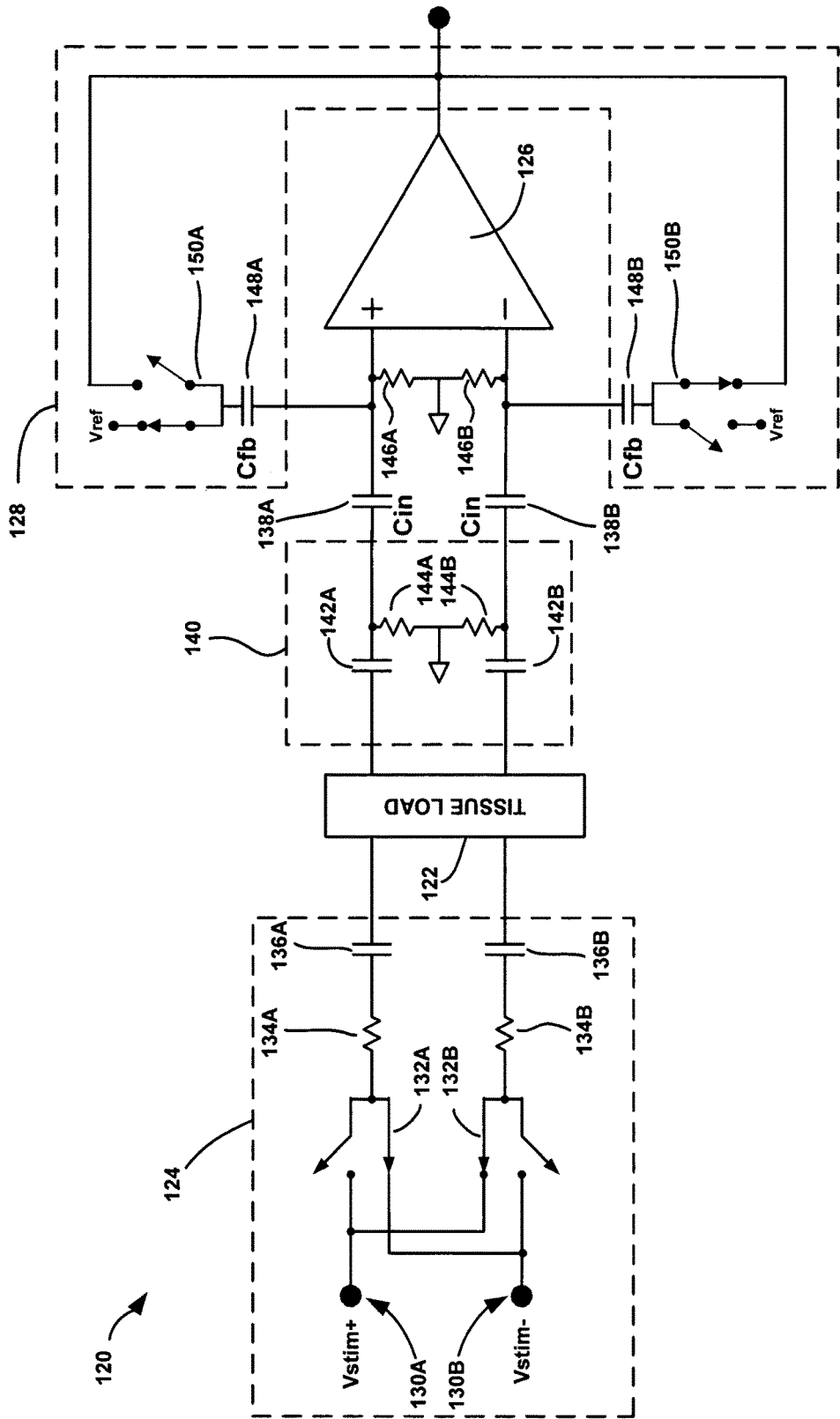
FIG. 9 is a circuit diagram illustrating an instrumentation amplifier for measuring impedance across a brain tissue load.

FIG. 9 is a circuit diagram illustrating an instrumentation amplifier 120 for measuring impedance across a tissue load 122. Tissue load 122 represents the tissue of a patient for which impedance is measured by instrumentation amplifier 120. Tissue 122 may be brain tissue. In general, it is important that instrumentation amplifier 120 does not stimulate excitable cells in the tissue or cause other detrimental effects such as electrode corrosion.

Instrumentation amplifier 120 may generally conform to instrumentation amplifier 80 described with reference to FIGS. 6-8. In the example of FIG. 9, instrumentation amplifier 120 applies synchronous detection principles to accurately measure the impedance of tissue load 122 with low power, inherent charge balancing, rejection of electrode potentials, and small stimulation currents. Instrumentation amplifier 120 is an example embodiment of previously described instrumentation amplifier 80. Like instrumentation amplifier 80, instrumentation amplifier 120 includes a front end 124, mixer amplifier 126, and feedback path 128. These features may generally correspond to front end 82, mixer amplifier 84, and feedback path 86 of instrumentation amplifier 80.

In FIG. 9, front end 124 includes input voltages Vstim+ and Vstim− at ports 130A and 130B (collectively referred to as "ports 130"), switches 132A and 132B (collectively referred to as "switches 132"), resistors 134A and 134B (collectively referred to as "resistors 134"), and capacitors 136A and 136B (collectively referred to as "capacitors 136"). In general, front end 124 modulates a stimulation current that creates a voltage on tissue load 122. The stimulation current may be applied across tissue load 122 via two or more electrodes, which may be mounted on one or more leads or carried on a surface of an implantable medical device housing. Similarly, the resulting voltage signal across tissue load 122 may be sensed by two or more electrodes deployed on one or more leads or on a device housing. The voltage on tissue load 122 is AC coupled to positive and negative inputs of mixer amplifier 126 by capacitors 138A and 138B (collectively referred to as "capacitors 138"), respectively. Thus, the tissue represented by tissue load 122 is not exposed to DC current. Moreover, the small modulated (AC) stimulation current, which may be approximately 10 µA or less, may not substantially excite the tissue represented by tissue load 122.

Switches 132 toggle between input voltages at ports 130 (Vstim+ and Vstim−) to generate stimulation current through resistor-capacitor (RC) pairs of resistor 134A and capacitor 136A and resistor 134B and capacitor 136B. Switches 132, resistors 134 and capacitors 136 may form an alternating current (AC) source that generates an ac stimulation current at a clock frequency for application to a load, such as 122. In particular, switches 132, resistors 134 and capacitors 136 form a modulator that modulates first and second voltages Vstim+ and Vstim− at the clock frequency to produce a chopped stimulation current for application to the load. The chopped stimulation current results in a chopped voltage signal across tissue load 122, which can then be used for impedance measurement. However, other types of ac current sources may be use to provide the ac stimulation current for impedance measurement.

The input voltages Vstim+ and Vstim− may be provided by regulated power supplies within a device in which instrumentation amplifier 120 is employed, such as an implantable medical device. Switches 132 open and close at a chopper frequency to, in effect, chop the input stimulation current delivered by input voltages at ports 130 via the RC pairs (134, 136) to measure tissue impedance. In this manner, front end 124 generates a modulated differential input signal that is processed by mixer amplifier 126 and feedback path 128. Stimulation currents at ports 130 may be provided by electrodes carried on leads that are connected to an electrical stimulator implanted within a patient. This is one example of delivery of stimulation current for impedance measurements. As an alternative, stimulation current for impedance measurement could be generated by one or more switched current sources. The reference voltages at ports 130 and the sizes of resistors 134 and capacitors 136 may be determined by the constraints on the stimulation current, linearity of the measurement, and the time constant of instrumentation amplifier 120 compared to the clock (not shown) that drives switches 132.

As an example, using a stimulation current of 10 μA, voltages at ports 130A and 130B may provide 2V and 0 V, respectively, and resistors 134 may be selected as 100 kΩ resistors. Alternatively, using 2000 kΩ resistors yields a 0.5 μA stimulation current with 100 kΩ resistors. Using 10 nF capacitors for capacitors 136 results in a stimulation current having a time constant of 1 ms, which requires a stimulation current with a frequency of approximately 5 kHz to ensure minimal error from settling dynamics. The nonlinearity of the measurement, assuming 1 kHz loads, is bounded to under 0.5% in this case.

If high pass filtering is desired, the input to mixer amplifier 126 may include a high pass filter 140 and coupling capacitors 138A, 138B. In FIG. 9, high pass filter 140 includes capacitors 142A, 142B (collectively referred to as "capacitors 142") and resistors 144A, 144B (collectively referred to as "resistors 144"). Resistors 146A and 146B (collectively referred to as "resistors 146") control the voltage at the input of mixer amplifier 126. Resistors 146 provide a DC conduction path that controls the voltage bias at the input of mixer amplifier 126. In other words, resistors 146 may be selected to provide an equivalent resistance that is used to keep the bias impedance high. Resistors 146 may, for example, be selected to provide a 5 GΩ equivalent resistor, but the absolute size of the equivalent resistor is not critical to the performance of instrumentation amplifier 120. In general, increasing the impedance improves the noise performance and rejection of harmonics, but extends the recovery time from an overload. To provide a frame of reference, a 5 GΩ equivalent resistor results in a referred-to-input (RTI) noise of approximately 20 nV/rt Hz with an input capacitance (Cin) of approximately 25 pF. In light of this, a stronger motivation for keeping the impedance high is the rejection of high frequency harmonics which can alias into the signal chain due to settling at the input nodes of mixer amplifier 126 during each half of a clock cycle.

Mixer amplifier 126 and feedback path 128 process the noisy modulated input signal to achieve a stable measurement of the differential voltage on tissue load 122 while operating at low power. Mixer amplifier 126 provides synchronous demodulation with respect to front end 82 and substantially eliminates noise, i.e., 1/f noise, popcorn noise, and offset, from the amplified output signal. Mixer amplifier 126 may be implemented using the modified folded-cascode architecture with switching at low impedance nodes.

As shown in FIG. 9, feedback path 128 includes top and bottom feedback path branches that provide negative feedback and a single-to-differential interface. The top and bottom feedback path branches include capacitors 148A and 148B (collectively referred to as "capacitors 148") which are connected to switches 150A and 150B (collectively referred to as "switches 150"), respectively. Switches 150A and 150B are 180 degrees out of phase with each other and toggle between the output of mixer amplifier 126 and a reference voltage (Vref) to modulate the output of mixer amplifier 126. Consequently, feedback path 128 provides negative feedback to keep the signal change at the input to mixer amplifier 126 small as previously described in this disclosure.

Switches 134, switches 150, and the switches at low impedance nodes in mixer amplifier 126 may be CMOS SPDT switches or other switches that provide fast switching dynamics. The transfer function of instrumentation amplifier 120 may be defined by the transfer function provided in equation (1) below, where Vout is the voltage of the output of mixer amplifier 126, Cin is the capacitance of input capacitors 138, ΔVin is the differential voltage at the inputs to mixer amplifier 126, Cfb is the capacitance of feedback capacitors 148, and Vref is the reference voltage that switches 150 mix with the output of mixer amplifier 126.

$$V\text{out} = C\text{in}(\Delta V\text{in})/C\text{fb} + V\text{ref} \quad (1)$$

From equation (1), it is clear that the gain of instrumentation amplifier 120 is set by the ratio of input capacitors Cin and feedback capacitors Cfb, i.e., capacitors 138 and capacitors 148. The ratio of Cin/Cfb may be selected to be on the order of 100. Capacitors 148 may be poly-poly, on-chip capacitors or other types of MOS capacitors and should be well matched, i.e., symmetrical. Capacitors 138 and 148 may be poly-poly capacitors or other types of MOS capacitors and should be well matched, i.e., symmetrical. Capacitors 138 and 148 may be placed on chip with the other instrumentation amplifier components.

In operation, instrumentation amplifier 120 may fold electromagnetic interference (EMI) into the modulated input signal at the carrier frequency and odd harmonics. In order to determine if the channel is corrupted, the output of instrumentation amplifier 120 can be monitored with no stimulation current applied to front end 124. Alternatively, spread-spectrum techniques may be used to break up the synchronous clock detection between front end 124 and mixer amplifier 126. Spread-spectrum clocking breaks up the uncorrelated noise into a broadband noise signal that is substantially eliminated by mixer amplifier 126, while maintaining the correlated impedance measurement.

The output of instrumentation amplifier 120 may be sent to an analog-to-digital converter (ADC) (not shown) that applies additional processing for measuring the impedance of tissue load 122. The ADC may be located within an impedance sensing module or within a processor of a medical device. Further, when instrumentation amplifier 120 is implanted within a patient, the tissue-electrode interface (front end 124) may be galvanically isolated from the measurement circuit (mixer amplifier 126 and feedback path 128). Isolation helps to reject electrode polarization and ensure net charge balance across the electrodes.

Figure 10:
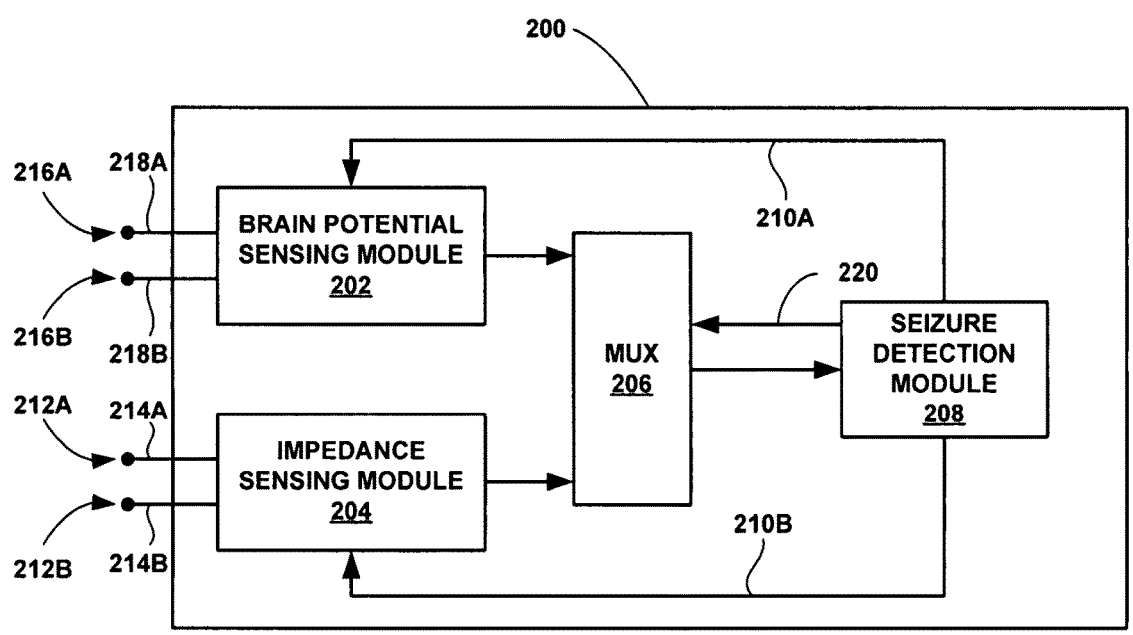
FIG. 10 is a block diagram illustrating a medical device that may be used to predict seizure in a patient by measuring an impedance and a potential of the brain of the patient.

FIG. 10 is a block diagram illustrating a medical device 200 that may be used to predict the onset of a seizure in a patient based on an impedance measurement of the brain of the patient and a measurement of an electrical potential of the brain. Example measurements of brain potential include EEG signals, ECoG signals, and other electrical signals that vary within the brain and indicate that the brain is in a state that indicates a possibility of an onset of a seizure. In general, medical device 200 may predict the onset of a seizure in a patient using a measurement of a brain potential in combination with any of the previously described techniques for predicting the onset of based on an impedance measurement of the brain of the patient. In different embodiments, the measured potential and measured impedance play different roles in the determination of whether the brain is in the state that indicates the possibility of a seizure. Some of the embodiments are described below. In each of the embodiments, however, medical device 200 measures an impedance of the brain of the patient and measures a brain potential of the patient, and predicts the onset of a seizure based on one or both of the measurements. In this way, medical device 200 may predict the onset of a seizure in a patient based on more than one parameter of the patient. In some embodiments, one type of measurements, i.e., impedance or brain potential, may be used to validate a brain seizure predicted based on the other type of measurement.

In the illustrated example of FIG. 10, medical device 200 includes brain potential sensing module 202, impedance sensing module 204, multiplexer (MUX) 206, and seizure detection module 208. Generally, medical device 200 may operate similar to medical devices 20, 56, and 70 in FIGS. 3, 4, and 5, respectively. That is, medical device 200 may be used during a first trial or learning stage to determine threshold values or trend templates to use for predicting the onset of seizures, or as an implantable medical device that predicts the onset of a seizure in a patient and takes some action in response to the seizure prediction. As previously described, the action may include delivering a therapy to the patient to prevent the onset of seizure or to otherwise mitigate the effects of the seizure or generating a notification to the patient or clinician that the seizure was predicted. Thus, although not illustrated in FIG. 10, medical device 200 may include one or more of a processor, memory, telemetry module, user interface, power source, therapy delivery module, and therapy elements that deliver stimulation or drug therapy to the patient. These components are not shown in FIG. 10 in the interest of simplicity and to avoid redundancy in this disclosure.

Impedance sensing module 204 corresponds to and, therefore, operates in a similar fashion as impedance sensing modules 22 and 58 that are previously described with respect to FIGS. 3, 4, and 5, respectively. In FIG. 10, impedance sensing module 204 includes circuitry, such as circuitry illustrated in FIG. 9, for measuring the impedance of the brain of a patient via electrodes 212A and 212B (collectively referred to as "electrodes 212"), which are coupled to impedance sensing module 204 via leads 214A and 214B, respectively. Electrodes 212 represent one or more sets of electrodes that may be implanted in one or more regions of the brain that are relevant to the occurrence of seizures, such as the cortex (e.g., front or motor cortex), brainstem, cranial nerves (e.g., the vagus nerve), or deep brain regions, such as the anterior thalamus, ventrolateral thalamus, globus pallidus, substantia nigra pars reticulata, subthalamic nucleus, neostriatum, cingulated gyrus or the cingulate gyrus.

As previously described, a low stimulation current, e.g., a stimulation current in a range of approximately 500 nA to approximately 10 µA, may be delivered across one or more regions of the brain via electrodes 212. Impedance sensing module 204 provides a measurement translating the impedance to an output voltage or current. When impedance sensing module 204 is implemented using the chopper stabilized instrumentation amplifier shown in FIGS. 6 and 7, the output is a relatively stable low noise signal with very low power requirements.

Brain potential sensing module 202 may include any suitable circuitry for measuring a brain potential, such as circuitry for EEG or ECoG. In an example embodiment, the circuitry of module 202 may include a chopper stabilized instrumentation amplifier, such as the chopper-stabilized instrumentation amplifier shown in FIGS. 6 and 7, to provide a stable, low noise signal with very low power requirements. In FIG. 10, brain potential sensing module 202 measures a brain potential via electrodes 216A and 216B (collectively referred to as "electrodes 216") which are coupled to module 202 via leads 218A and 218B, respectively. As with electrodes 212, electrodes 216 represent one or more sets of electrodes. That is, in other embodiments, brain potential sensing module 202 may sense a potential of the brain of the patient via any suitable number of electrodes. One or more of the electrodes 216 may also be positioned on a housing of medical device 200. Electrodes 216 may be implanted and/or external to the patient. For example, electrodes 216 may be placed externally on the scalp of the patient to obtain EEG data. Alternatively, electrodes 216 may be implanted subdurally or in the cerebral cortex of the brain to obtain ECoG data, or other brain potentials that can be measured to predict the onset seizures. As yet another alternative, electrodes 216 may include a set of implanted electrodes and a set of external electrodes attached to a scalp of the patient.

In embodiments in which electrodes 216 are implanted in a patient, electrodes 216 may be positioned in one or more regions of a brain of a patient in order to measure the potential of the one or more regions. Example regions include cortex (e.g., front or motor cortex), brainstem, cranial nerves (e.g., the vagus nerve), or deep brain regions, such as the anterior thalamus, ventrolateral thalamus, globus pallidus, substantia nigra pars reticulata, subthalamic nucleus, neostriatum, cingulated gyrus or the cingulate gyrus.

Electrodes 212 for measuring an impedance of the brain and electrodes 216 for measuring the potential of the brain may or may not be positioned in the same region of the brain of the patient. The impedance may be more revealing of a brain state indicative of a seizure in certain brain regions, while the potential may be more revealing in other brain regions, which may be different than that for the impedance measurements. Thus, in some embodiments, electrodes 212 and 216 are positioned in separate parts of the brain (or external to the brain in the case of electrodes 216). However, in some embodiments, electrodes 212 and 216 may be implanted in the same region of the brain, in which case, a single set of electrodes may be coupled to brain potential sensing module 202 and impedance sensing module 204. Other potential sensing electrode 16 arrangements may also be used.

As with some embodiments of medical devices 20, 56, and 70, medical device 200 may, in some embodiments, include internal and external components. That is, in some embodiments, impedance sensing module 204, brain potential sensing module 202, MUX 206, and/or seizure detection module 208 may be in different housings in order to allow some of the components to remain external to the patient while other components are implanted. For example, in embodiments in which electrodes 212 are coupled to impedance sensing module 204 and implanted within the patient, but electrodes 216 are attached to an external surface of the patient, impedance sensing module 204 may be in a separate housing from brain potential sensing module 202. In such embodiments, impedance sensing module 204 may be implanted within the patient and telemetrically coupled to an external housing carrying brain potential sensing module 202 and other components necessary for the operation of medical device 200 as described.

Impedance sensing module 204 and brain potential sensing module 202 are coupled to seizure detection module 208 through MUX 206. MUX 206 selectively applies the output of brain potential sensing module 202 and impedance sensing module 204 to seizure detection module 208. In particular, MUX 206 may apply the output of modules 202 and 204 to seizure detection module 208 at substantially the same time, in an alternating fashion, in a pattern other than an alternating pattern, or under the control or request of seizure detection module 208.

In the example of FIG. 10, seizure detection module 208 controls MUX 206 via control signal 220, brain potential sensing module 202 via control signal 210A, and impedance sensing module 204 via control signal 210B. Control signals 210A and 210B turn brain potential sensing module 202 and impedance sensing module 204, respectively, on and off. That is, controls signals 210A and 210B control when modules 202 and 204, respectively, operate. Control signal 220 controls MUX 206 to apply the output of one or both of modules 202 and 204 to seizure detection module 208. In some embodiments, seizure detection module 208 may actively operate of modules 202, 204 and/or include separate ports to receive signals from modules 202, 204, in which cases MUX 206 may or may not be necessary.

In general, seizure detection module 208 determines whether the brain is in a state indicative of a possibility of a seizure based on the output of one or both of brain potential sensing module 202 and impedance sensing module 204. In one embodiment, seizure detection module 208 detects the onset of a seizure based on the output of both of modules 202 and 204. In this example embodiment, seizure prediction module 208 may monitor the output of one of modules 202 and 204 and, in response to detecting onset of a seizure based on the one output, requests MUX 206, via control signal 220, to apply the other output. As an example, MUX 206 may apply the output of impedance sensing module 204 to seizure detection module 208 until seizure detection module 208 detects the onset of a seizure based on the output of module 204. Seizure detection module 208 may process the measured impedance using any one of the techniques described above in order to determine whether the measured impedance indicates the brain is in a state in which a seizure is possible. Until seizure detection module 208 detects an impedance measurement that indicates an onset of a seizure is likely, seizure detection module 208 may send control signal 210A to brain potential sensing module 202 to cause module 202 to enter a sleep mode to conserve power.

Upon determining that the impedance measurements indicate a seizure is likely, seizure detection module 208 may then send control signal 220 to MUX 206 to cause MUX 206 to awake brain potential sensing module 202 and apply the output of brain potential sensing module 202 to its input. At substantially the same time, seizure detection module 208 may send control signal 210B to impedance sensing module 204 to cause module 204 to enter a sleep state or mode to conserve power. Seizure detection module 208 processes the output of module 202 to validate the initial seizure prediction determination based on the measured impedance. In particular, seizure detection module 208 determines whether the potential measurements also indicate the brain is in the state in which a seizure is likely.

Seizure detection module 208 may employ techniques for determining whether the measured potential indicates the brain is in the state in which a seizure is likely that are similar to described above with respect to determining whether measured impedance indicates the brain is in the state. For example, in one embodiment, seizure detection module 208 compares an amplitude of the measured potential signal to a predetermined threshold. The relevant amplitude may be, for example, the instantaneous amplitude of an incoming potential signal or an average amplitude of the potential over period of time. In one embodiment, the threshold value is determined during the trial phase that precedes implantation of a chronic therapy delivery device within the patient.

In another embodiment, seizure detection module 208 correlates a pattern of the measured potential to a pattern template. If the pattern of the measured potential correlates well, i.e., matches, the pattern template, the measured potential indicates the brain is in the state that indicates a seizure is likely. In some embodiments, the template matching algorithm that is employed to determine whether the pattern matches the template (10) may not require a one hundred percent (100%) correlation match, but rather may only match some percentage of the pattern. For example, if the measured potential values exhibit a pattern that matches about 75% or more of the template, the algorithm may determine that there is a substantial match between the pattern and the template. The pattern template may be generated in a trial phase, such as by the potential activity prior to, and possibly during or after, an actual seizure. In one embodiment, a pattern for potential values that characterize a brain state that will likely lead to a seizure is a rate of change of the potential measurements over time. For example, a positive increase in the time rate of change (i.e., the slope or first derivative) of the potential measurements may indicate a likelihood of a seizure, although a decrease (negative slope) in rate of change or another pattern may also be indicative of the likelihood of a seizure. Alternatively, a time rate of change (i.e., the slope) of the potential measurements that matches or exceeds the time rate of change of the template may indicate a likelihood of a seizure. The exact trend that is indicative of a brain state in which a seizure is likely may be determined during a trial phase, as with the measured impedance processing techniques described above.

The measured potential signal from brain potential sensing module 202 may be analyzed for slope, amplitude, temporal correlation or frequency correlation with a template signal, or combinations thereof. The slope, amplitude, temporal correlation or frequency correlation with a template signal may be similar to the techniques described above with respect to determining whether the measured impedance indicates the brain is in the state that indicates a seizure is likely to occur.

When seizure detection module 208 determines the output of module 202 indicates a seizure is likely, seizure detection module 208 takes an action. The action may be at least one of sending a signal to memory (not shown) to record data related to the seizure, control a therapy delivery module (not shown) to deliver therapy to the patient or generate a notification to the patient or clinician. However, if seizure detection module 208 determines that the measured potential does not validate the initial seizure prediction made based on the measured impedance, seizure detection module 208 concludes that a seizure is not detected. Thus, in some embodiments, both the measured impedance from impedance sensing module 204 and the measured potential from brain potential sensing module 202 must indicate that an onset of a seizure is likely in order for seizure detection module 208 to conclude that the brain is in the state that indicates the possibility of a seizure. If only one of the measured impedance or the measured potential suggests the seizure is likely, module 208 may send a signal to memory to record data (e.g., the signals from impedance sensing module 204 that suggested the brain was in the state in which the seizure was likely and/or the signals from brain potential sensing module 202 that indicated a seizure was not likely) as a flagged event. The data may be stored for later retrieval and analysis by a clinician to review the source of the anomaly between the impedance and potential measurements.

In other embodiments in which the measured impedance and the measured potential must both indicate that an onset of a seizure is likely in order for seizure detection module 208 to conclude that the brain is in the state that indicates the possibility of a seizure, seizure detection module 208 may initially monitor the signal from brain potential sensing module 202, rather than impedance sensing module 204 as in the previous embodiment. If seizure detection module 208 finds that the measured potential from brain potential sensing module 202 suggests the brain is in the state that indicates a likelihood of seizure, seizure detection module 208 may validate (or confirm) the initial determination by controlling MUX 208 to apply the output of impedance sensing module 204 to seizure detection module 208. Seizure detection module 208 may then process the signal from impedance sensing module 204 to validate the initial seizure prediction, and conclude that the brain is in the state indicative of a seizure. If the measured impedance does not support such a conclusion, seizure detection module 208 concludes that the brain is not in the state indicative of the seizure.

In another embodiment, seizure detection module 208 determines whether the brain is in the state indicative of a possibility of a seizure based on the output of one or both of modules 202 and 204. In this embodiment, an output from one of brain potential sensing module 202 or impedance sensing module 204 may control the seizure prediction. Seizure detection module 208 makes an initial determination of whether the brain is in the state indicative of the possibility of the seizure based on either the measured potential from brain potential sensing module 202 or the measured impedance from impedance sensing module 204. Upon making the initial seizure prediction, seizure detection module 208 may determine whether the other signal (i.e., either the signal indicative of measured impedance or brain potential) on which the initial determination was not based also indicates an onset of a seizure is possible. Thus, seizure detection module 208 may attempt to validate the initial seizure prediction. However, rather than concluding that the seizure is not likely if the second signal fails to validate the initial determination, the initial determination controls, and seizure detection module 208 sends a signal to memory (not shown) to record data related to the seizure, controls a therapy delivery module (not shown) to deliver therapy to the patient or generates a notification to the patient or clinician. In this case, if validation fails, seizure detection module 208 may nevertheless proceed with therapy but flag the recorded data so that a clinician can review the anomalous differences between the impedance and potential measurements, in terms of seizure indication.

In another embodiment, seizure detection module 208 determines whether the brain is in the state indicative of a seizure based on the output of one or both of modules 202 and 204. In this embodiment, an output from one of brain potential sensing module 202 or impedance sensing module 204 may control the seizure prediction. As one example, MUX 206 may apply the outputs of modules 202 and 204 to seizure detection module 208 in an alternating fashion. In this example, modules 202 and 204 may operate at substantially the same time and MUX 206 may toggle between their outputs. Alternatively, seizure detection module 208 may control the operation of modules 202 and 204 via control signals 210A and 210B, respectively. In such an example, MUX 206 may be removed from medical device 200. In any case, seizure detection module 208 receives the output of modules 202 and 204 in an alternating fashion. In other embodiments, seizure detection module 208 may receive the output of modules 202 and 204 in another pattern, such as, but not limited to two or more outputs from module 204 for a single output from brain potential sensing module 202.

Seizure detection module 208 processes the received output signal using any of the previously described techniques, i.e., any of the previously described techniques for detecting onset of a seizure based on an impedance measurement or based on a measurement of a brain potential, such as a measurement of an EEG signal or ECoG signal. Seizure detection module 208 may output a signal that causes medical device 200 to take action in response to detecting onset of seizure based on the output of either of modules 202 and 204. Alternatively, seizure detection module 208 may output a signal to take action in response to detecting onset of a seizure based on consecutively received signals from modules 202 and 204.

The pattern exhibited by the measured impedance relative to the measured potential may be indicative of a brain state in which a seizure is likely to occur. For example, an increase in an amplitude of the impedance signal from impedance sensing module 204 and a subsequent (in time) decrease in the amplitude of the potential signal from brain potential sensing module 202 may indicate the brain state in which a seizure is likely to occur. However, other patterns and more complex patterns are possible. A pattern (or "trend") template may be generated during a trialing stage, in which the measured impedance and measured potential signals are correlated with an actual seizure in order to determine if a pattern, if any, is correlated with the occurrence of the seizure. If a pattern that indicates the brain state in which a seizure is likely to occur is generated during the trialing stage, the pattern may be stored within a memory of medical device 200 for use by seizure detection module 208. Seizure detection module 208 may then use any of the template matching techniques to determine whether a pattern in the signal from impedance sensing module 204 relative to the signal from the brain potential sensing module 202 indicate the brain is in the state in which a seizure is likely to occur. Examples of suitable template matching techniques include the ones described above with respect to predicting a seizure based on an impedance measurement or a potential measurement.

As another example, MUX 206 may apply the outputs of modules 202 and 204 to seizure detection module at substantially the same time. It is recognized that MUX 206 and control signals 210A and 210B may be removed from medical device 200 in this example. In this example, brain potential sensing module 202 and impedance sensing module 204 operate at the same time and seizure detection module 208 monitors the outputs of modules 202 and 204 at substantially the same time. In this example, seizure detection module 208 may detect the onset of a seizure in a similar fashion with respect to the previous example, but monitors the output of modules 202 and 204 at substantially the same time instead of in an alternating fashion. That is, seizure detection module 208 monitors the output of modules 202 and 204 at substantially the same time and detects the onset of a seizure when the output of one of the modules indicates a seizure or when the output of both modules indicate the onset of seizure at substantially the same time. However, in some cases, the stimulation current delivered to brain tissue by impedance sensing module 204 for measuring impedance may interfere with the brain potential measurements. Brain potential sensing module 202 may be calibrated to generate a signal indicative of the potential of the brain by taking into consideration the impedance-measuring stimulation current delivered by impedance sensing module 204.

In summary, one of modules 202, 204 may be used as a primary triggering device for seizure prediction. If one of modules 202, 204 indicates a seizure, the other device may be used to validate the seizure. If validation succeeds, therapy and/or data recording is applied. If validation fails, there are several possibilities. First, if validation fails, seizure detection module 208 may nevertheless proceed with therapy delivery (or adjustment) and/or data recording, but flag the event for later review in view of the differences between the outputs of the modules 202, 204. Alternatively, if validation fails, seizure detection module 208 may withhold delivery (or adjustment) of therapy and flag the event for later review in view of the differences between the outputs of modules 202, 204. In some embodiments, both modules 202, 204 may be monitored on an alternating basis, or one of the modules may serve as a primary source that is monitored on continuing basis while the other module is only monitored for validation purposes. In each case, the module 202, 204 that is not being monitored at a given time may be turned off or its output may be ignored. When its output is needed, a module 202, 204 may be activated by seizure detection module 208. In other embodiments, more than two modules 202, 204 may be applied to support more complex validation or analysis. For example, impedance, EEG signals, and ECoG signals could be monitored simultaneously, on an alternating basis, or for validation purposes.

Certain advantages may be provided by the various embodiments described in FIG. 10. As an example, processing the output of only one of modules 202 and 204 at any give time may consume less power and result in a shorter latency between receiving the signal and detecting onset of a seizure than is possible when the output of modules 202 and 204 are processed at substantially the same time.

Although brain potential sensing module 202 and impedance sensing module 204 are shown to be two separate modules in the embodiment of medical device 200 shown in FIG. 10, in other embodiments, brain potential sensing module 202 and impedance sensing module 204 may be incorporated into a common sensing module that is coupled to seizure detection module 208. Brain potential sensing module 202 and impedance sensing module 204 may share circuitry or have separate circuitry.

Figure 11:
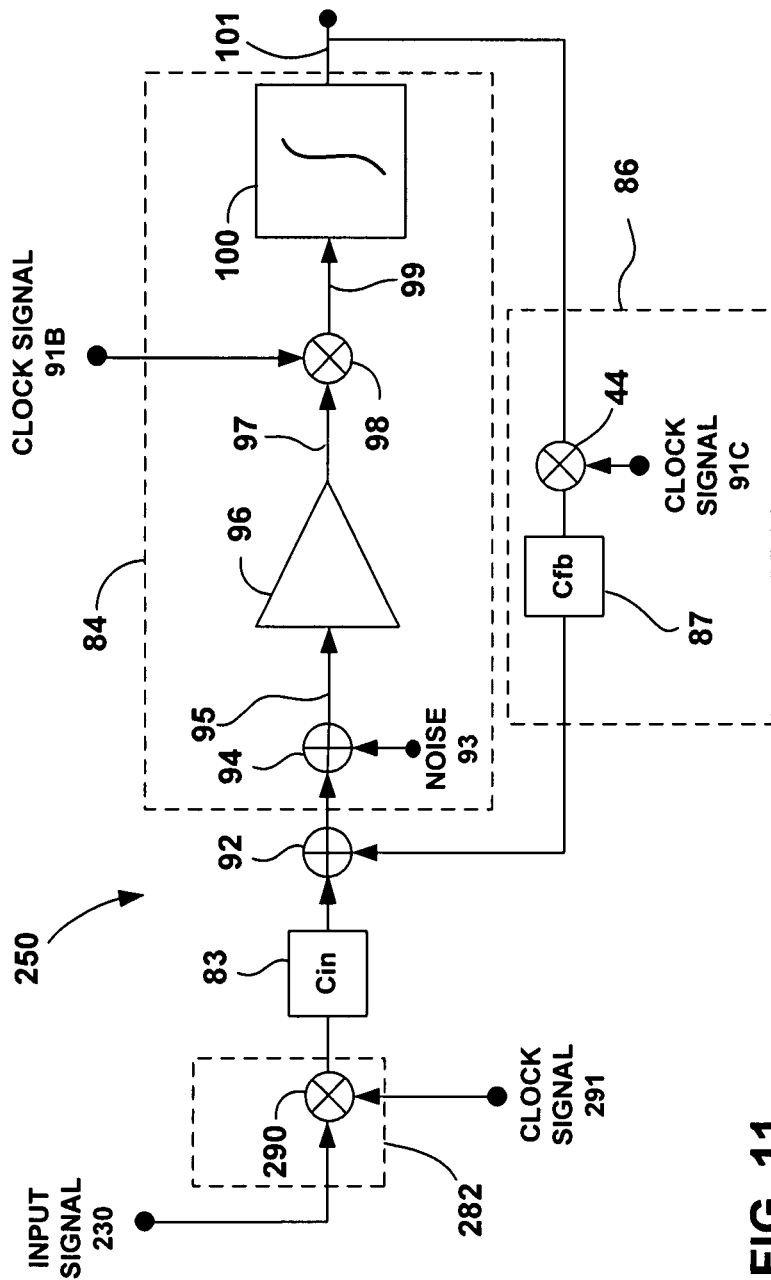
FIG. 11 is a diagram illustrating a signal flow path of a brain potential sensing module of the medical device in FIG. 10.

FIG. 11 is a diagram illustrating a signal flow path for a chopper stabilized instrumentation amplifier 250 that brain potential sensing module 202 may include to generate a signal indicative of a measured potential of brain tissue. The signal flow diagram for instrumentation amplifier 250 may be substantially the same as that for instrumentation amplifier 80 in FIG. 7, but with a different front end. Accordingly similar numbered components in FIG. 11 and FIG. 7 share similar functionality. In the interest of brevity and to avoid redundancy, the signal flow through mixer amplifier 84 and feedback path 86 is not described in detail. Instead, the flow of input signal 230 through front end 282 is described.

In FIG. 11, front end 282 includes a modulator 290 for modulating an input signal 230 to produce modulated input signal 291. Front end 282 may be coupled to a physiological sensor that generates an input signal 230 proportional to a sensed physiological parameter at its outputs. For example, input signal 230 may be a differential output signal from a pair of electrodes attached to an external surface of a patient or implanted within the brain of a patient, e.g., a pair of electrodes that sense EEG or ECoG signals.

Modulator 290 modulates a differential amplitude of input signal 230 to a carrier frequency provided by clock signal 291. Clock signal 291, like other clock signals described in this disclosure, may be a square wave signal that effectively multiples the signal by plus 1 and minus 1 at a desired clock frequency and is synchronous with clock signals 91B and 91C. In this manner, modulator 290 chops the input signal 230 prior to application of the input signal to mixer amp 84. Modulator 290 may, in some embodiments, comprise a pair of complementary metal oxide semiconductor (CMOS) single pole, double throw (SPDT) switches that are driven by clock signal 291 to modulate (chop) input signal 230 to the carrier frequency. The CMOS SPDT switches may be coupled to a set of differential capacitors to form a continuous time switched capacitor network that forms input capacitance Cin at the input of mixer amplifier 84. Additionally, the CMOS SPDT switches may be cross-coupled to each other to reject common mode As previously described with respect to FIG. 7, summing node 24 introduces offset and 1/f noise into the signal at the input to mixer amplifier 84 and mixer amplifier 84 produces a stable, low noise output signal. Mixer amplifier 84 may be implemented using the circuit illustrated in FIG. 8. Feedback path 86 provides negative feedback that keeps the signal change small at the input to mixer amplifier 84 and, thus, substantially eliminates glitching that would otherwise result from the limited bandwidth of mixer amplifier 84.

Figure 12:
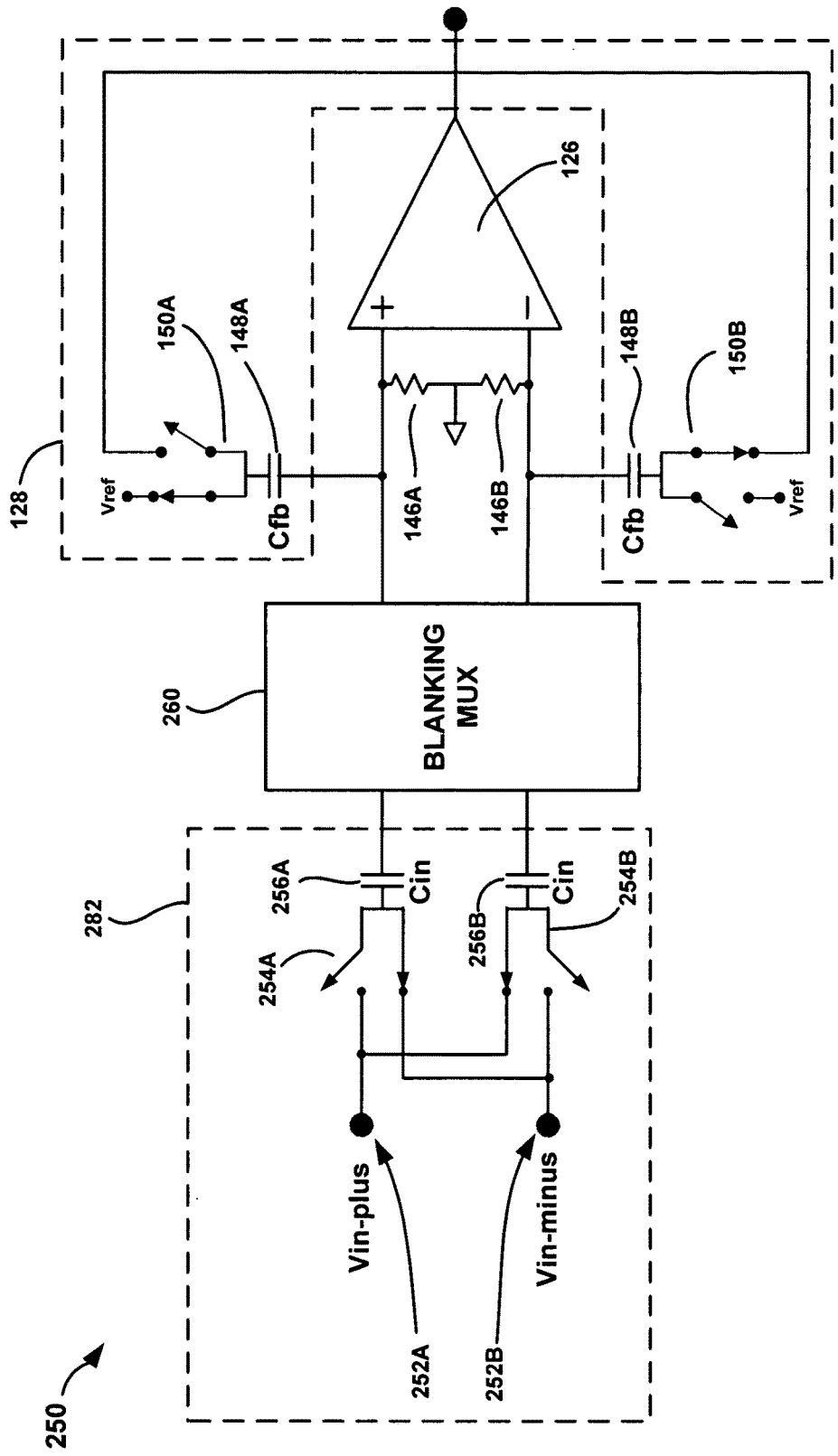
FIG. 12 is a circuit diagram illustrating a chopper-stabilized instrumentation amplifier that may be incorporated into the brain potential sensing module.

FIG. 12 is a circuit diagram illustrating chopper-stabilized instrumentation amplifier 250. The architecture of instrumentation amplifier 250 may be substantially similar to instrumentation amplifier 120 shown in FIG. 9. Accordingly, similar numbered components in FIG. 12 and FIG. 9 exhibit similar functionality.

In FIG. 12, instrumentation amplifier 250 receives a differential voltage across its inputs 252A and 252B (collectively referred to as "inputs 252"). Inputs 252A and 252B provide voltages Vin-plus and Vin-minus, respectively. For example, inputs 252 may be coupled to a pair of sensing electrodes, such as a pair of electrodes attached to an external surface of a patient or implanted within a region of the brain of the patient that generate EEG or ECoG signals.

Inputs 252A and 252B are connected to capacitors 256A and 256B (collectively referred to as "capacitors 256") through switches 254A and 254B (collectively referred to as "switches 254"), respectively. Switches 2504 are driven by a clock signal provided by a system clock (not shown) and are cross-coupled to each other to reject common-mode signals. Capacitors 256 are coupled at one end to a corresponding one of switches 254 and to a corresponding input of mixer amplifier 126 at the other end. In particular, capacitor 256A is coupled to the positive input of mixer amplifier 126, and capacitor 126B is coupled to the negative input of amplifier 126, providing a differential input.

In FIG. 12, switches 254 and capacitors 256 form front end 282, which operates as a continuous time switched capacitor network as previously described with respect to FIG. 11. Switches 254 toggle between an open state and a closed state in which inputs 252 are coupled to capacitors 256 at a clock frequency to modulate (chop) the signal at inputs 252 to the carrier (clock) frequency. As previously described, the signal at inputs 252 may be a low frequency signal within a range of approximately 0 Hz to approximately 100 Hz. The carrier frequency may be within a range of approximately 4 kHz to approximately 10 kHz. Hence, the low frequency sensor output is chopped to the higher chop frequency band.

Switches 254 toggle in-phase with one another to provide a differential input signal to mixer amplifier 126. During a first phase of the clock signal, switch 254A connects input 252B to capacitor 256A and switch 254B connects input 252A to capacitor 256B. During a second phase, switches 254 change state such that switch 254A couples input 252A to capacitor 256A and switch 254B couples input 252B to capacitor 256B. Switches 254 synchronously alternate between the first and second phases to modulate the differential voltage at inputs 252 at the carrier frequency. The resulting chopped differential signal is applied across capacitors 256, which couple the differential signal across the inputs of mixer amplifier 126. Resistors 146, mixer amplifier 126, and feedback path 128 operate as previously described with respect to FIG. 9.

As further shown in FIG. 12, for applications in which instrumentation amplifier 250 provides an output in conjunction with a stimulation current being supplied to instrumentation amplifier 120 (FIG. 9), blanking circuitry may be added to instrumentation amplifier 250 between coupling capacitors 256 and the inputs to mixer amplifier 126 to ensure that the input signal settles before reconnecting mixer amplifier 126 to front end 282. For example, the blanking circuitry may be a blanking multiplexer (MUX) 260 that selectively couples and de-couples mixer amplifier 126 from front end 282. This blanking circuitry selectively decouples the mixer amplifier from the differential input signal and selectively disables the first and second modulators, i.e., switches 254, 150, e.g., during delivery of a stimulation current to instrumentation amplifier 120 which may be incorporated in impedance measurement module 204.

Blanking MUX 260 is optional, but may be desirable in some cases. The clocks driving switches 254, 150 to function as modulators cannot be simply shut off because residual offset voltage on mixer amplifier 126 may saturate the amplifier in a few milliseconds. For this reason, blanking MUX 260 may be provided to decouple amplifier 126 from the input signal for a specified period of time during and following application of a stimulation by a cardiac pacemaker or defibrillator, or by a neurostimulator.

To achieve suitable blanking, the input and feedback switches 254, 150 should be disabled while mixer amplifier 126 continues to demodulate the input signal. This holds the state of the integrator within mixer amplifier 126 because the modulated signal is not present at the inputs of the integrator, while the demodulator continues to chop the DC offsets. Accordingly, blanking MUX 260 may further include circuitry or be associated with circuitry configured to selectively disable switches 254, 150 during a blanking interval. Post blanking, mixer amplifier 126 may require additional time to resettle because some perturbations may remain. Thus, the total blanking time includes time for demodulating the input signal while the input and switches 254, 250 are disabled and time for settling of any remaining perturbations. An example blanking time following application of a stimulation pulse may be approximately 8 ms with 5 ms for mixer amplifier 126 and 3 ms for the AC coupling components.

Figure 13:
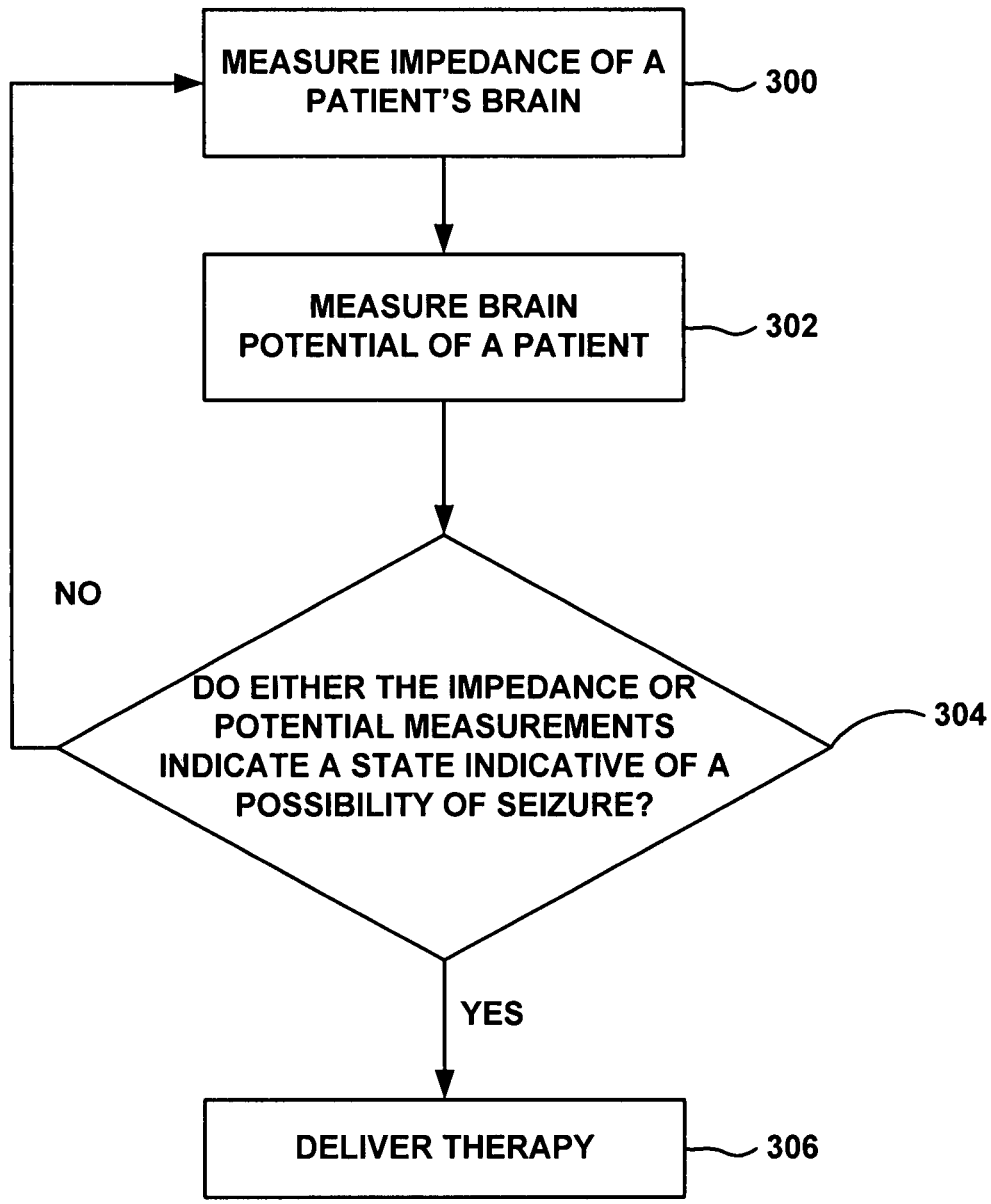
FIG. 13 is flow diagram illustrating a method for predicting seizure in a patient based on an impedance measurement of the brain and a measurement of a brain potential.

FIG. 13 is flow diagram illustrating a method for predicting seizure in a patient using one of an impedance measurement of a brain of a patient or measurement of a brain potential of the patient. The method illustrated in FIG. 13 may be implemented using medical device 200 and circuitry described in this disclosure. As shown in FIG. 13, the method begins by measuring an impedance of a patient's brain (300) and measuring a brain potential of a patient (302). The impedance measurement and measurement of the brain potential may be obtained at the substantially the same time, in an alternating fashion, or in another pattern.

After the measurements have been obtained, any of the previously described techniques, e.g., correlation techniques, template matching techniques, thresholding techniques, and the like, may be used to determine whether either the measured impedance or the measured potential indicate the brain is in a state indicative of a possibility of a seizure (304). If the measurements were obtained at substantially the same time, separate techniques may be applied to each of the measurement in parallel or, alternatively, the techniques may be applied one after the other. As an alternative, if the measurements were obtained in an alternating fashion, the detection techniques may be applied in an alternating fashion as well. That is, after the impedance measurement is obtained, a correlation technique may be applied to the impedance measurement. While the correlation technique is executing, the measurement of the brain potential may be obtained. In this way, the measurements and processing techniques are performed in an alternating fashion.

When the seizure detection technique does not detect onset of a seizure, the method loops and steps 300, 302, and 304 are repeated. However, if the onset of a seizure is detected based on either of the measurements, therapy is delivered to treat the seizure. The therapy may be stimulation therapy, drug therapy, or a combination of both as described in this disclosure.

Figure 14:
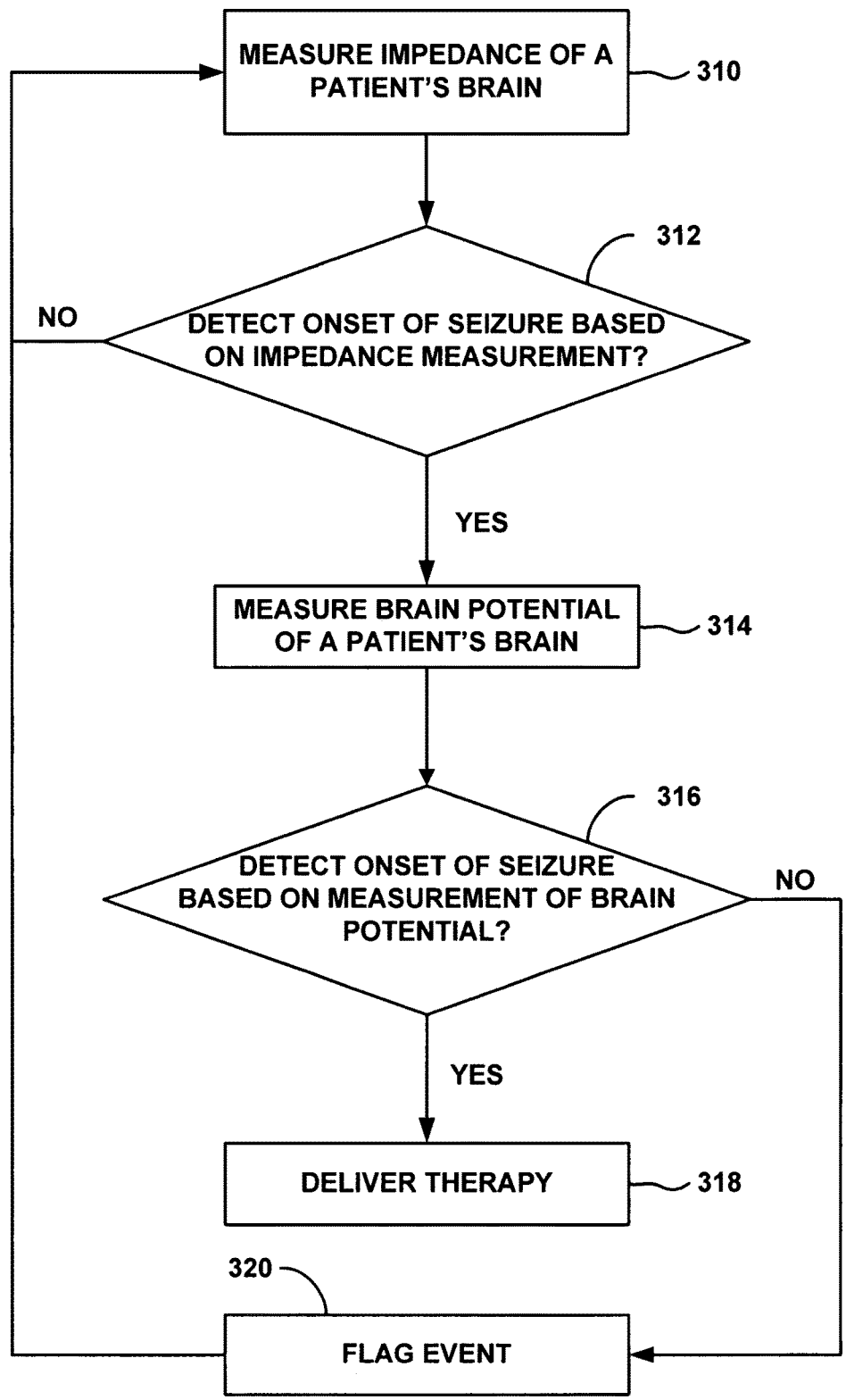
FIG. 14 is flow diagram illustrating another method for predicting seizure in a patient based on an impedance measurement of the brain and a measurement of a brain potential.

FIG. 14 is a flow diagram illustrating another technique for predicting a seizure in a patient based on an impedance measurement of the brain of a patient and a measurement of a brain potential of a patient. The technique illustrated in FIG. 14 may be implemented using medical device 200 and circuitry described in this disclosure. In the technique shown in FIG. 14, seizure detection module 208 (FIG. 10) determines that the brain of the patient is in a state indicative of a possibility of a seizure based on an initial seizure prediction based on measured impedance that is validated by a seizure prediction based on measured potential. In other embodiments, the initial seizure prediction may be based on the measured potential and validated with the measured impedance. As shown in FIG. 14, seizure detection module 208 (or another processor) measures an impedance of a patient's brain (310) and applying one of the previously described techniques to detect an onset of a seizure based on the impedance measurement (312). If the measured impedance indicates that an onset of a seizure is not likely, seizure detection module 208 continues measuring the impedance of the brain (310). In this way, seizure detection module 208 monitors an impedance of the patient's brain until the impedance measurement indicates the onset of a seizure.

When the measured impedance indicates that the brain is in the state in which a seizure is likely, seizure detection module 208 measures a brain potential of the patient (314) and applying any of the previously mentioned techniques to detect onset of a seizure based on the measured potential (316). If seizure detection module 208 determines the measured potential indicates an onset of a seizure is likely, therapy is delivered to treat the seizure as previously described in this disclosure (318). Alternatively, data may be recorded in a memory of medical device 200 or seizure detection module 208 may generate a notification to a patient or clinician. If seizure detection module 208 determines that the measured potential does not indicate an onset of a seizure is likely, seizure detection module 208 flags the event for further analysis (e.g., by a clinician) (320). Flagging the event may involve storing the impedance and brain potential measurements and other data obtained at the time the measurements were taken. The method in FIG. 14 may decrease false positives by using a second measurement, e.g., a measurement of a brain potential or measurement of other electrical signal that indicates the onset of seizure, as a validation or confirmation step.

Figure 15:
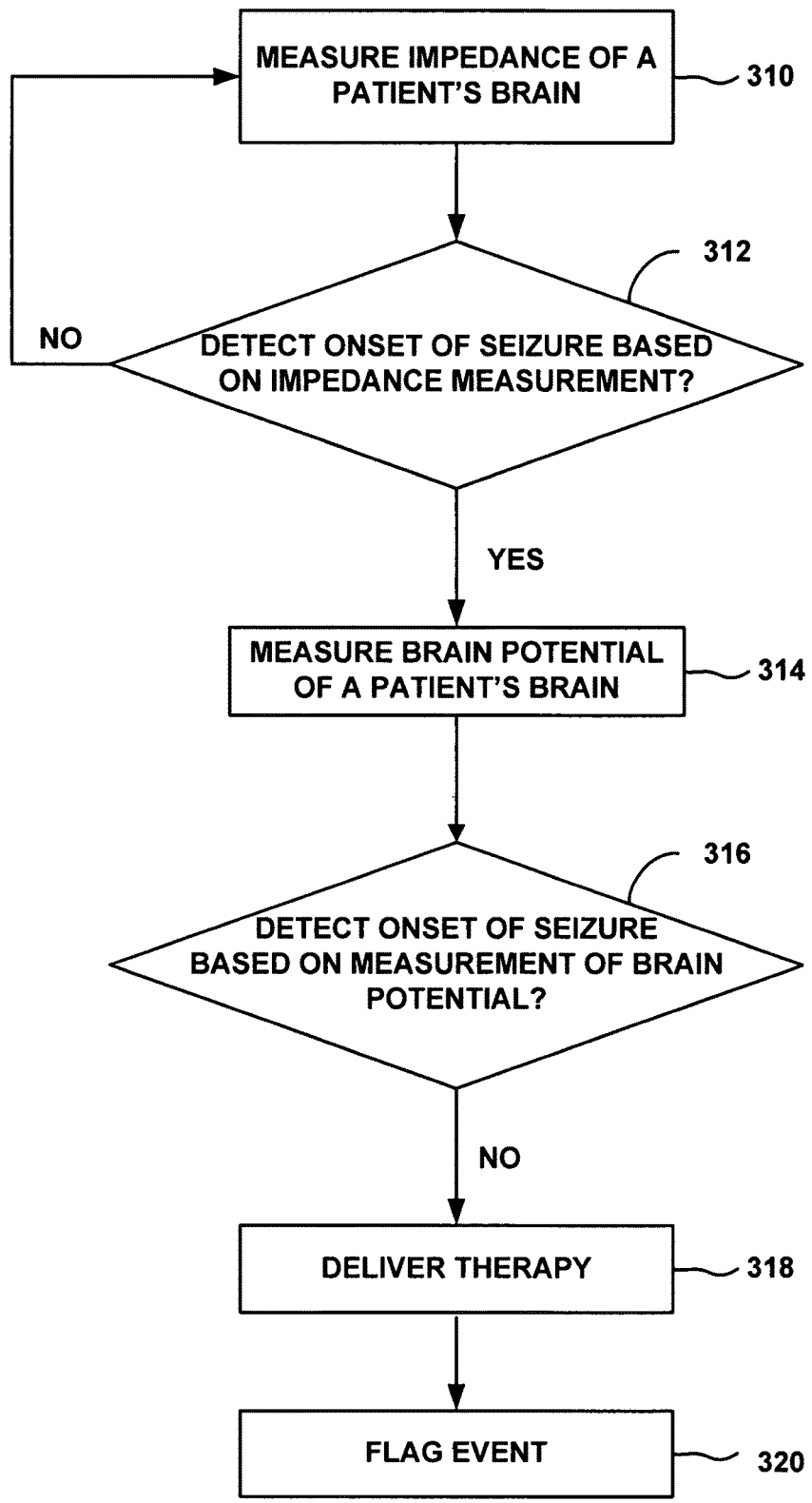
FIG. 15 is flow diagram illustrating another method for predicting seizure in a patient based on an impedance measurement of the brain and a measurement of a brain potential.

FIG. 15 is a flow diagram illustrating another technique for predicting a seizure in a patient based on an impedance measurement of the brain of a patient and a measurement of a brain potential of a patient. The technique illustrated in FIG. 15 is substantially similar to that shown in FIG. 14, but rather than flagging an event if an initial seizure prediction is not validated, seizure detection module 208 merely attempts to validate the initial seizure prediction. In the technique shown in FIG. 15, seizure detection module 208 measures impedance of the patient's brain (310), determines that the brain of the patient is in a state indicative of a possibility of a seizure based on an initial seizure prediction based on measured impedance (312), measures a potential of the brain (314), and attempts to validate the initial seizure prediction based on measured potential. If the potential measurements indicate that the brain is not in a state indicative of a possibility of a seizure (316), seizure prediction module 208 delivers therapy (318) and flags the event (320). In some embodiments, however, seizure prediction module 208 does not flag the event.

Various embodiments of the invention have been described. The invention may be embodied as a computer-readable medium that includes instructions to cause a processor to perform any of the methods described herein. These and other embodiments are within the scope of the following claims.

The invention claimed is:

1. A method comprising:
receiving, with a processor, impedance measurements indicative of an impedance of a brain of a patient, wherein the impedance of the brain is indicative of a physiological state of the brain;
determining, with the processor, a trend in the impedance measurements over time;
determining, with the processor, that the brain is in a state indicative of a possibility of a future seizure based on the trend; and
controlling, with the processor, delivery of therapy to the patient based on determining that the brain is in the state indicative of the possibility of the future seizure.

2. The method of claim 1, further comprising measuring the impedance of the brain of the patient with an impedance sensing module, wherein measuring the impedance of the brain of the patient comprises delivering a stimulation current in a range of about 500 nanoamps to about 10 microamps across tissue in one or more regions of the brain of the patient.

3. The method of claim 1, further comprising, with the processor, comparing an amplitude of at least one of the impedance measurements to a predetermined threshold and determining that the brain is in the state indicative of the possibility of the future seizure based on the comparison.

4. The method of claim 3, wherein comparing the amplitude of the at least one of the impedance measurements to the predetermined threshold value comprises comparing an average amplitude of a plurality of the impedance measurements over a period of time to the predetermined threshold value.

5. The method of claim 1, further comprising:
with the processor, comparing the trend to a template; and based on the comparison of the trend to the template, determining the trend substantially correlates to the template, wherein determining that the brain is in the state indicative of the possibility of the future seizure comprises determining that the brain is in the state indicative of the possibility of a future seizure based on determining the trend substantially correlates to the template.

6. The method of claim 5, wherein determining the trend substantially correlates to the template comprises determining a first frequency component of the trend substantially correlates to a second frequency component of the template.

7. The method of claim 1, wherein the trend indicates a rate of change of the impedance measurements over time.

8. The method of claim 1, wherein controlling delivery of therapy comprises at least one of controlling delivery of a pharmaceutical agent or controlling delivery of electrical stimulation to tissue of the patient.

9. The method of claim 1, further comprising, with the processor, controlling the therapy to inhibit an onset of the future seizure.

10. The method of claim 1, further comprising, with the processor, controlling the therapy to reduce severity or duration of the future seizure.

11. The method of claim 1, wherein the state indicative of the possibility of a future seizure is a first state, the method further comprising, with the processor, controlling the therapy to return the brain to a second state indicative of a lower possibility of the future seizure than the first state.

12. The method of claim 1, further comprising measuring the impedance of the brain of the patient with an impedance sensing module, wherein measuring the impedance comprises measuring a complex impedance over at least one frequency.

13. The method of claim 12, wherein the at least one frequency is in a range of approximately 1 kilohertz to approximately 100 kilohertz.

14. The method of claim 13, wherein the at least one frequency is in a range of approximately 4 kilohertz to approximately 16 kilohertz.

15. The method of claim 1, further comprising measuring the impedance of the brain of the patient with an impedance sensing module, wherein measuring the impedance of the brain of the patient comprises measuring the impedance within at least two regions of the brain.

16. The method of claim 15, wherein the at least two regions are selected from a group comprising: a cortex, brainstem, anterior thalamus, ventrolateral thalamus, globus pallidus, substantia nigra pars reticulata, subthalamic nucleus, neostriatum, cingulated gyrus or cingulate gyrus.

17. The method of claim 1, further comprising measuring the impedance of the brain of the patient with an impedance sensing module, wherein measuring the impedance of the brain of the patient comprises measuring the impedance within at least one of a cortex, brainstem, anterior thalamus, ventrolateral thalamus, globus pallidus, substantia nigra pars reticulata, subthalamic nucleus, neostriatum, cingulated gyrus or cingulate gyrus.

18. The method of claim 1, further comprising, with the processor, generating a notification based on determining that the brain is in the state indicative of the possibility of the future seizure.

19. The method of claim 1, further comprising measuring the impedance of the brain of the patient with an impedance sensing module, wherein measuring the impedance of the brain of the patient comprises:

generating an alternating current (ac) stimulation current at a frequency;

applying the stimulation current to a brain tissue load to produce an input signal;

amplifying the input signal to produce an amplified signal;

demodulating the amplified signal at the frequency to produce an output signal;

modulating an amplitude of the output signal at the frequency to produce a feedback signal; and applying the feedback signal to the input signal via a first feedback path.

20. The method of claim 19, wherein the input signal comprises a differential input signal.

21. A system comprising:
an impedance sensing module configured to measure an impedance of a brain of a patient, and generate impedance measurements indicative of the impedance of the brain, wherein the impedance of the brain is indicative of a physiological state of the brain;

a processor coupled to the impedance sensing module, wherein the processor is configured to receive impedance measurements from the impedance sensing module, determine a trend in the impedance measurements over time, and determine that the brain is in a state indicative of a possibility of a future seizure based on the trend; and a therapy delivery module coupled to the processor, wherein the processor is configured to control delivery of therapy to the patient via the therapy delivery module in response to determining that the brain is in the state indicative of the possibility of the future seizure.

22. The system of claim 21, wherein the therapy comprises at least one of delivery of a pharmaceutical agent or electrical stimulation.

23. The system of claim 21, wherein the state indicative of the possibility of the future seizure is a first state, and wherein the processor is configured to control the therapy to return the brain to a second state indicative of a lower possibility of the future seizure than the first state.

24. The system of claim 21, wherein the impedance sensing module is configured to deliver a stimulation current in a range of about 500 nanoamps to about 10 microamps across tissue in one or more regions of the brain of the patient to measure the impedance.

25. The system of claim 21, wherein the processor is further configured to compare an amplitude of at least one of the impedance measurements to a predetermined threshold and determine the brain is in the state indicative of the possibility of the future seizure based on the comparison and the trend.

26. The system of claim 21, wherein the processor is further configured to compare the trend to a template, determine the trend substantially correlates to the template based on the comparison, and determine the brain is in the state indicative of the possibility of the future seizure based on determining the trend substantially correlates to the template.

27. The system of claim 26, wherein the processor is configured to determine the trend substantially correlates to the template by at least determining a first frequency component of the trend substantially correlates to a second frequency component of the template.

28. The system of claim 21, wherein the trend indicates a rate of change of the measured impedance over time.

29. The system of claim 21, wherein the impedance sensing module is configured to measure the impedance of the brain and generate the impedance measurements by at least measuring a complex impedance over at least one frequency.

30. The system of claim 29, wherein the at least one frequency is in a range of approximately 1 kilohertz to approximately 100 kilohertz.

31. The system of claim 21, wherein the impedance sensing module is configured to measure the impedance within at least two regions of the brain and generate the impedance measurements based on the impedance measured within at least two regions of the brain.

32. The system of claim 21, wherein the impedance sensing module is configured to measure the impedance within at least one of a cortex, brainstem, anterior thalamus, ventrolateral thalamus, globus pallidus, substantia nigra pars reticulata, subthalamic nucleus, neostriatum, cingulated gyrus or cingulate gyrus of the brain.

33. The system of claim 21, further comprising a notification device, wherein the processor is configured to activate the notification device in response to determining the brain is in the state indicative of the possibility of the future seizure.

34. The system of claim 21, wherein the impedance sensing module comprises a chopper-stabilized instrumentation amplifier comprising:
an alternating current (ac) source configured to generate an ac stimulation current at a frequency for application to a brain tissue load;

a mixer amplifier coupled to receive an input signal from the brain tissue load in response to the stimulation current, wherein the mixer amplifier is configured to amplify the input signal to produce an amplified signal and demodulate the amplified signal at the frequency to produce an output signal;

a modulator configured to modulate an amplitude of the output signal at the frequency; and a feedback path configured to apply the modulated output signal as a feedback signal to the input signal.

35. The system of claim 34, wherein the input signal comprises a differential input signal.

36. The system of claim 21, further comprising one or more electrodes implantable in the brain of the patient, wherein the impedance sensing module is configured to deliver an electrical stimulus to the brain via at least one of the one or more electrodes to measure the impedance of the brain and generate the impedance measurements indicative of the impedance of the brain.

37. A system comprising:
means for measuring an impedance of a brain of a patient, wherein the impedance of the brain is indicative of a physiological state of the brain;

means for generating impedance measurements of the brain of the patient based on the measured impedance;

means for determining a trend in the impedance measurements over time;

means for determining that the brain is in a state indicative of a possibility of a future seizure based on the trend; and means for delivering therapy to the patient in response to the means for determining that the brain is in the state indicative of the possibility of the future seizure.

38. The system of claim 37, further comprising means for providing a notification to the patient in response to the means for determining that the brain is in the state indicative of the possibility of the future seizure.

39. The system of claim 37, wherein the means for determining that the brain is in the state indicative of the possibility of the future seizure comprises:
  means for comparing the trend to a template and determining the trend substantially correlates to a template; and
  means for determining the brain is in the state indicative of the possibility of the future seizure based on the determining the trend substantially correlates to the template.

40. The system of claim 37, further comprising:
  means for comparing an amplitude of at least one of the impedance measurements to a predetermined threshold value; wherein the means for determining that the brain is in the state indicative of the possibility of the future seizure determines that the brain is in the state indicative of the possibility of the future seizure based on the comparison and the trend.

41. The system of claim 37, wherein the means for measuring the impedance of the brain of the patient comprises a chopper-stabilized instrumentation amplifier comprising:
  means for generating an alternating current (ac) stimulation current at a frequency for application to a brain tissue load, wherein the application of the stimulation current to the brain tissue load produces an input signal;
  means for amplifying the input signal to produce an amplified signal;
  means for demodulating the amplified signal at the frequency to produce an output signal;
  means for modulating an amplitude of the output signal at the frequency; and
  means for applying the modulated output signal as a feedback signal to the input signal.

42. The system of claim 41, wherein the input signal comprises a differential input signal.

43. A non-transitory computer-readable medium comprising instructions that cause a programmable processor to:
  receive impedance measurements indicative of an impedance of a brain of a patient, wherein the impedance of the brain is indicative of a physiological state of the brain;
  determine a trend in the impedance measurements over time;
  determine that the brain is in a state indicative of a possibility of a future seizure based on the trend; and
  control a therapy delivery module to deliver therapy to the patient based on determining that the brain is in the state indicative of the possibility of the future seizure.

44. The non-transitory computer-readable medium of claim 43, further comprising instructions that cause the programmable processor to:
  compare an amplitude of at least one of the impedance measurements to a predetermined threshold value, wherein the instructions that cause the programmable processor to determine that the brain is in the state indicative of the possibility of the future seizure cause the programmable processor to determine that the brain is in the state indicative of the possibility of the future seizure based on the comparison and the trend.

45. The non-transitory computer-readable medium of claim 43, further comprising instructions that cause the programmable processor to compare the trend to a template, wherein the instructions that cause the programmable processor to determine that the brain is in the state indicative of the possibility of the future seizure based on the trend comprise instructions that cause the programmable processor to determine that the brain is in the state indicative of the possibility of a future seizure based on that the trend substantially correlates to the template.

46. A method comprising:
  generating, with an impedance sensing module, impedance measurements indicative of an impedance of a brain of a patient, wherein the impedance of the brain is indicative of a physiological state of the brain;
  detecting, with a seizure detection module, an occurrence of a seizure;
  associating, with a processor, the occurrence of the seizure with a plurality of the impedance measurements indicative of the impedance of the brain during a period of time beginning before the occurrence of the seizure;
  determining, with the processor, a trend in the plurality of impedance measurements over time;
  subsequent to determining the trend in the plurality of impedance measurements over time, receiving, with the processor, additional impedance measurements indicative of an impedance of the brain of the patient
  determining, with the processor, the trend in the additional impedance measurements over time;
  determining, with the processor, that the brain is in a state indicative of a possibility of a future seizure based on determining the trend in the additional impedance measurements; and
  controlling, with the processor, delivery of therapy to the patient based on determining that the brain is in the state indicative of the possibility of the future seizure.

47. The method of claim 46, wherein detecting the occurrence of the seizure comprises analyzing electroencephalogram data or electrocorticogram data.

48. The method of claim 46, further comprising determining, with the processor, a threshold value that indicates the brain is in the state indicative of the possibility of the future seizure based on the plurality of impedance measurements indicative of the impedance of the brain during the period of time beginning before the occurrence of the seizure.

49. The method of claim 48, wherein determining the threshold value comprises determining a lowest impedance measurement of the plurality of impedance measurements associated with the occurrence of the seizure.

50. The method of claim 46, wherein the period of time begins before the occurrence of the seizure and ends at an onset of the seizure.

51. The method of claim 46, further comprising, with the impedance sensing module, measuring the impedance of the brain of the patient, wherein measuring the impedance of the brain of the patient comprises measuring the impedance within at least two regions of the brain.

52. The method of claim 46, further comprising generating a template based on the trend in the plurality of impedance measurements.

53. A system comprising:
  an impedance sensing module configured to generate impedance measurements indicative of an impedance of a brain of a patient, wherein the impedance of the brain is indicative of a physiological state of the brain;
  a seizure detection module configured to detect an occurrence of a seizure;
  a processor coupled to the impedance sensing module and the seizure detection module, wherein the processor is configured to associate the occurrence of the seizure with a plurality of the impedance measurements indicative of the impedance of the brain during a period of time beginning before the occurrence of the seizure, determine a trend in the plurality of impedance measurements over time, receive additional impedance measurements indicative of an impedance of the brain of the patient subsequent to determining the trend in the plurality of impedance measurements over time, determine the trend in the additional impedance measurements over time, and determine that the brain is in a state indicative of a possibility of a future seizure based on determining the trend in the additional impedance measurements; and a therapy delivery module coupled to the processor, wherein the processor is configured to control delivery of therapy to the patient via the therapy delivery module in response to determining that the brain is in the state indicative of the possibility of the future seizure.

54. The system of claim 53, wherein the seizure detection module is configured to monitor electrical activity of the brain via at least one of electroencephalography or electrocorticography to detect the occurrence of the seizure.

55. The system of claim 53, wherein the processor is configured to determine a threshold value that indicates the brain is in the state indicative of the possibility of the future seizure based on the plurality of impedance measurements indicative of the impedance of the brain during the period of time beginning before the occurrence of the seizure.

56. The system of claim 53, wherein the processor is configured to generate a template based on the trend in the plurality of impedance measurements.

* * * * *